United States Patent
Linder et al.

(10) Patent No.: US 11,701,218 B2
(45) Date of Patent: Jul. 18, 2023

(54) SOFT TISSUE TO BONE REPAIR DEVICES, SYSTEMS, AND METHODS

(71) Applicant: CONEXTIONS, INC., Salt Lake City, UT (US)

(72) Inventors: Richard J. Linder, Sandy, UT (US); Erik N. Kubiak, Las Vegas, NV (US); Scott D. Miles, Sandy, UT (US); Tyler J. Cole, Sandy, UT (US); Roy M. Taylor, Salt Lake City, UT (US); Shawn P. Reese, Salt Lake City, UT (US)

(73) Assignee: CoNextions, Inc., Salt Lake City, UT (US)

( * ) Notice: Subject to any disclaimer, the term of this patent is extended or adjusted under 35 U.S.C. 154(b) by 246 days.

(21) Appl. No.: 16/546,622

(22) Filed: Aug. 21, 2019

(65) Prior Publication Data
US 2020/0038170 A1    Feb. 6, 2020

Related U.S. Application Data

(63) Continuation of application No. 14/885,956, filed on Oct. 16, 2015, now Pat. No. 10,390,935, which is a
(Continued)

(51) Int. Cl.
*A61F 2/08* (2006.01)
*A61B 17/064* (2006.01)
(Continued)

(52) U.S. Cl.
CPC .......... *A61F 2/0811* (2013.01); *A61B 17/064* (2013.01); *A61B 17/07292* (2013.01);
(Continued)

(58) Field of Classification Search
CPC ............ A61F 2/0811; A61F 2002/0888; A61F 2002/0858; A61F 2002/0864;
(Continued)

(56) References Cited

U.S. PATENT DOCUMENTS

| 3,166,072 A | 1/1965 | Sullivan et al. |
| 4,388,926 A | 6/1983 | Shalaby et al. |

(Continued)

FOREIGN PATENT DOCUMENTS

| WO | WO2016061530 | 4/2016 |
| WO | WO2016138033 | 9/2016 |

OTHER PUBLICATIONS

McKenzie, "An Experimental Multiple Barbed Suture For The Long Flexor Tendons Of The Palm And Fingers," Journal of Bone and Joint Surgery, Aug. 1967, pp. 440-447, vol. 49 B, No. 3.
(Continued)

*Primary Examiner* — Jennifer Dieterle
*Assistant Examiner* — Melissa A Hoban
(74) *Attorney, Agent, or Firm* — David L. Stott

(57) ABSTRACT

Devices, systems and methods for fixating soft tissue to bone. In one embodiment, a repair device system for fixating soft tissue to bone includes a carrier member, multiple anchors, and a bone anchor. The carrier member includes multiple pad portions and a bone coupling portion. Each of the pad portions are aligned with an adjacent pad portion. The pad portions are configured to be positioned over a side of the soft tissue and the bone coupling portion is coupled to the multiple pad portions. Each anchor is sized and configured to extend through the at least one opening defined in one of the multiple pad portions and through the soft tissue. The bone anchor is configured to be coupled to the bone coupling portion and configured to be secured to the bone.

16 Claims, 14 Drawing Sheets

Related U.S. Application Data continuation-in-part of application No. 13/953,709, filed on Jul. 29, 2013, now Pat. No. 9,427,309.

(60) Provisional application No. 62/064,533, filed on Oct. 16, 2014, provisional application No. 61/804,570, filed on Mar. 22, 2013, provisional application No. 61/677,239, filed on Jul. 30, 2012.

(51) Int. Cl.

| | | |
|---|---|---|
| *A61B 17/072* | (2006.01) | |
| *A61B 17/08* | (2006.01) | |
| *A61B 17/11* | (2006.01) | |
| *A61B 17/04* | (2006.01) | |
| *A61B 17/00* | (2006.01) | |

(52) U.S. Cl.
CPC .......... *A61B 17/08* (2013.01); *A61B 17/1146* (2013.01); *A61B 17/0487* (2013.01); *A61B 2017/00867* (2013.01); *A61B 2017/0496* (2013.01); *A61B 2017/0641* (2013.01); *A61B 2017/1103* (2013.01); *A61B 2017/1132* (2013.01); *A61F 2002/0829* (2013.01); *A61F 2002/0858* (2013.01); *A61F 2002/0864* (2013.01); *A61F 2002/0876* (2013.01); *A61F 2002/0888* (2013.01)

(58) Field of Classification Search
CPC ..... A61F 2002/0876; A61F 2002/0829; A61B 17/064; A61B 17/07292; A61B 17/08; A61B 17/1146; A61B 17/0487; A61B 2017/00867; A61B 2017/0496; A61B 2017/0641; A61B 2017/1103; A61B 2017/1132

See application file for complete search history.

(56) References Cited

U.S. PATENT DOCUMENTS

| | | | |
|---|---|---|---|
| 4,414,967 A | | 11/1983 | Shapiro |
| 4,454,875 A | * | 6/1984 | Pratt ........................ F16B 15/02 606/219 |
| 4,461,298 A | | 7/1984 | Shalaby et al. |
| 4,469,101 A | | 9/1984 | Coleman et al. |
| 4,489,875 A | | 12/1984 | Crawford et al. |
| 4,532,926 A | | 8/1985 | O'Holla |
| 4,534,350 A | | 8/1985 | Golden et al. |
| 4,548,202 A | | 10/1985 | Duncan |
| 4,610,250 A | | 9/1986 | Green |
| 4,655,222 A | * | 4/1987 | Florez ................. A61B 17/0644 606/219 |
| 4,655,980 A | | 4/1987 | Chu |
| 4,741,330 A | | 5/1988 | Hayhurst |
| 4,776,890 A | | 10/1988 | Chu |
| 4,796,612 A | | 1/1989 | Reese |
| 4,810,549 A | | 3/1989 | Abrams et al. |
| 4,873,976 A | | 10/1989 | Schreiber |
| 4,942,875 A | | 7/1990 | Hlavacek et al. |
| 4,946,467 A | | 8/1990 | Ohi et al. |
| 4,960,420 A | | 10/1990 | Goble et al. |
| 4,983,184 A | | 1/1991 | Steinemann |
| 4,997,433 A | * | 3/1991 | Goble ................... A61F 2/0811 606/62 |
| 5,047,103 A | | 9/1991 | Abrams et al. |
| 5,061,283 A | | 10/1991 | Silvestrini |
| 5,163,956 A | | 11/1992 | Liu et al. |
| 5,207,841 A | | 5/1993 | Abrams |
| 5,209,756 A | | 5/1993 | Seedhom et al. |
| 5,250,049 A | | 10/1993 | Michael |
| 5,290,552 A | | 3/1994 | Sierra et al. |
| 5,292,334 A | | 3/1994 | Howansky |
| 5,306,290 A | | 4/1994 | Martins et al. |
| 5,306,500 A | | 4/1994 | Rhee et al. |
| 5,312,023 A | | 5/1994 | Green et al. |
| 5,326,013 A | | 7/1994 | Green et al. |
| 5,329,943 A | | 7/1994 | Johnson |
| 5,342,376 A | | 8/1994 | Ruff |
| 5,346,746 A | | 9/1994 | Abrams |
| 5,370,662 A | | 12/1994 | Stone et al. |
| 5,389,098 A | | 2/1995 | Tsuruta et al. |
| 5,413,791 A | | 5/1995 | Rhee et al. |
| 5,446,091 A | | 8/1995 | Rhee et al. |
| 5,447,265 A | | 9/1995 | Vidal et al. |
| 5,458,636 A | | 10/1995 | Brancato |
| 5,465,894 A | | 11/1995 | Clark et al. |
| 5,480,644 A | | 1/1996 | Freed |
| 5,510,418 A | | 4/1996 | Rhee et al. |
| 5,523,348 A | | 6/1996 | Rhee et al. |
| 5,527,341 A | | 6/1996 | Gogolewski et al. |
| 5,542,594 A | | 8/1996 | McKean et al. |
| 5,556,428 A | | 9/1996 | Shah |
| 5,575,803 A | | 11/1996 | Cooper et al. |
| 5,580,923 A | | 12/1996 | Yeung et al. |
| 5,603,443 A | | 2/1997 | Clark et al. |
| 5,607,094 A | | 3/1997 | Clark et al. |
| 5,630,824 A | | 5/1997 | Hart |
| 5,630,842 A | | 5/1997 | Brodniewicz |
| 5,649,937 A | | 7/1997 | Bito et al. |
| 5,665,112 A | | 9/1997 | Thal |
| 5,667,839 A | | 9/1997 | Berg |
| 5,706,997 A | | 1/1998 | Green et al. |
| 5,711,472 A | | 1/1998 | Bryan |
| 5,713,903 A | | 2/1998 | Sander et al. |
| 5,716,981 A | | 2/1998 | Hunter et al. |
| 5,723,008 A | | 3/1998 | Gordon |
| 5,728,110 A | | 3/1998 | Vidal et al. |
| 5,732,871 A | | 3/1998 | Clark et al. |
| 5,756,678 A | | 5/1998 | Shenoy et al. |
| 5,766,250 A | | 6/1998 | Chervitz et al. |
| 5,785,713 A | * | 7/1998 | Jobe ................. A61B 17/0401 606/75 |
| 5,800,544 A | | 9/1998 | Demopulos et al. |
| 5,807,581 A | | 9/1998 | Rosenblatt et al. |
| 5,858,156 A | | 1/1999 | Abrams et al. |
| 5,860,229 A | | 1/1999 | Morgenstern |
| 5,865,361 A | | 2/1999 | Milliman et al. |
| 5,908,427 A | | 6/1999 | McKean et al. |
| 5,916,224 A | | 6/1999 | Esplin |
| 5,947,999 A | * | 9/1999 | Groiso ................. A61F 2/0811 606/219 |
| 5,961,520 A | | 10/1999 | Beck, Jr. et al. |
| 5,964,774 A | | 10/1999 | McKean et al. |
| 5,980,524 A | | 11/1999 | Justin et al. |
| 5,997,811 A | | 12/1999 | Esposito |
| 6,010,764 A | | 1/2000 | Abrams |
| 6,013,083 A | | 1/2000 | Bennett |
| 6,027,523 A | | 2/2000 | Schmieding |
| 6,030,410 A | | 2/2000 | Zurbrugg |
| 6,045,560 A | | 4/2000 | McKean et al. |
| 6,079,606 A | | 6/2000 | Milliman et al. |
| 6,080,192 A | | 6/2000 | Demopulos et al. |
| 6,083,242 A | | 7/2000 | Cook |
| 6,083,332 A | | 7/2000 | Abrams |
| 6,086,547 A | | 7/2000 | Hanssen et al. |
| 6,099,538 A | | 8/2000 | Moses et al. |
| 6,106,556 A | | 8/2000 | Demopulos et al. |
| 6,110,560 A | | 8/2000 | Abrams |
| 6,111,165 A | | 8/2000 | Berg |
| 6,206,886 B1 | | 3/2001 | Bennett |
| 6,241,139 B1 | | 6/2001 | Milliman et al. |
| 6,241,747 B1 | | 6/2001 | Ruff |
| 6,250,532 B1 | | 6/2001 | Green et al. |
| 6,277,394 B1 | | 8/2001 | Sierra |
| 6,330,965 B1 | | 12/2001 | Milliman et al. |
| 6,333,347 B1 | | 12/2001 | Hunter et al. |
| 6,358,557 B1 | | 3/2002 | Wang et al. |
| 6,383,199 B2 | | 5/2002 | Carter et al. |
| 6,413,742 B1 | | 7/2002 | Olsen et al. |
| D462,766 S | | 9/2002 | Jacobs et al. |
| 6,464,706 B1 | | 10/2002 | Winters |
| 6,472,171 B1 | | 10/2002 | Toman et al. |

(56) References Cited

U.S. PATENT DOCUMENTS

| | | | |
|---|---|---|---|
| 6,485,503 B2 | 11/2002 | Jacobs et al. | |
| 6,491,714 B1 | 12/2002 | Bennett | |
| 6,495,127 B1 | 12/2002 | Wallace et al. | |
| 6,515,016 B2 | 2/2003 | Hunter | |
| 6,517,579 B1 | 2/2003 | Paulos et al. | |
| 6,533,802 B2 | 3/2003 | Bojarski et al. | |
| 6,544,273 B1 | 4/2003 | Harari et al. | |
| 6,551,315 B2 | 4/2003 | Kortenbach et al. | |
| 6,569,186 B1 | 5/2003 | Winters et al. | |
| 6,575,976 B2 | 6/2003 | Grafton | |
| 6,644,532 B2 | 11/2003 | Green et al. | |
| 6,645,226 B1 | 11/2003 | Jacobs et al. | |
| 6,648,893 B2 | 11/2003 | Dudasik | |
| 6,652,563 B2 | 11/2003 | Dreyfuss | |
| 6,656,183 B2 | 12/2003 | Colleran et al. | |
| 6,656,215 B1 * | 12/2003 | Yanez | A61F 2/064 |
| | | | 623/1.13 |
| 6,666,873 B1 | 12/2003 | Cassell | |
| 6,669,073 B2 | 12/2003 | Milliman et al. | |
| 6,689,803 B2 | 2/2004 | Hunter | |
| 6,712,830 B2 | 3/2004 | Esplin | |
| 6,716,226 B2 | 4/2004 | Sixto, Jr. et al. | |
| 6,740,100 B2 | 5/2004 | Demopulos et al. | |
| 6,743,233 B1 | 6/2004 | Baldwin et al. | |
| 6,743,240 B2 | 6/2004 | Smith et al. | |
| 6,773,450 B2 | 8/2004 | Leung et al. | |
| 6,824,548 B2 | 11/2004 | Smith et al. | |
| 6,830,174 B2 | 12/2004 | Hillstead et al. | |
| 6,843,794 B2 | 1/2005 | Sixto, Jr. et al. | |
| 6,877,647 B2 | 4/2005 | Green et al. | |
| 6,893,452 B2 | 5/2005 | Jacobs | |
| 6,905,513 B1 | 6/2005 | Metzger | |
| 6,945,979 B2 | 9/2005 | Kortenbach et al. | |
| 6,953,138 B1 | 10/2005 | Dworak et al. | |
| 6,953,139 B2 | 10/2005 | Milliman et al. | |
| 6,962,594 B1 | 11/2005 | Thevenet | |
| 6,991,643 B2 | 1/2006 | Saadat | |
| 7,016,194 B1 | 3/2006 | Wong | |
| 7,056,331 B2 | 6/2006 | Kaplan et al. | |
| 7,070,602 B2 | 7/2006 | Smith et al. | |
| 7,074,203 B1 | 7/2006 | Johanson et al. | |
| 7,090,685 B2 | 8/2006 | Kortenbach et al. | |
| 7,121,446 B2 | 10/2006 | Arad et al. | |
| 7,129,209 B2 | 10/2006 | Rhee | |
| 7,156,862 B2 | 1/2007 | Jacobs et al. | |
| 7,172,615 B2 | 2/2007 | Morriss et al. | |
| 7,176,256 B2 | 2/2007 | Rhee et al. | |
| 7,189,238 B2 | 3/2007 | Lombardo et al. | |
| 7,226,468 B2 | 6/2007 | Ruff | |
| 7,229,413 B2 | 6/2007 | Violante et al. | |
| 7,232,445 B2 | 6/2007 | Kortenbach et al. | |
| 7,275,674 B2 | 10/2007 | Racenet et al. | |
| 7,296,724 B2 | 11/2007 | Green et al. | |
| 7,303,107 B2 | 12/2007 | Milliman et al. | |
| 7,303,577 B1 * | 12/2007 | Dean | A61B 17/0401 |
| | | | 606/151 |
| 7,309,346 B2 | 12/2007 | Martinek | |
| 7,328,829 B2 | 2/2008 | Arad et al. | |
| 7,343,920 B2 | 3/2008 | Toby et al. | |
| 7,354,627 B2 | 4/2008 | Pedrozo et al. | |
| 7,398,907 B2 | 7/2008 | Racenet et al. | |
| 7,401,720 B1 | 7/2008 | Durrani | |
| 7,438,209 B1 | 10/2008 | Hess et al. | |
| 7,442,202 B2 | 10/2008 | Dreyfuss | |
| 7,464,848 B2 | 12/2008 | Green et al. | |
| 7,510,566 B2 | 3/2009 | Jacobs et al. | |
| 7,530,484 B1 | 5/2009 | Durrani | |
| 7,530,990 B2 | 5/2009 | Perriello et al. | |
| 7,565,993 B2 | 7/2009 | Milliman et al. | |
| 7,568,604 B2 | 8/2009 | Ehrenfels et al. | |
| 7,600,663 B2 | 10/2009 | Green | |
| 7,604,151 B2 | 10/2009 | Hess et al. | |
| 7,611,038 B2 | 11/2009 | Racenet et al. | |
| 7,611,521 B2 | 11/2009 | Lubbers et al. | |
| 7,615,058 B2 | 11/2009 | Sixto, Jr. et al. | |
| 7,624,487 B2 | 12/2009 | Trull et al. | |
| 7,635,074 B2 | 12/2009 | Olson et al. | |
| 7,635,367 B2 * | 12/2009 | Groiso | A61B 17/0642 |
| | | | 606/75 |
| 7,640,617 B2 | 1/2010 | Kennedy et al. | |
| 7,641,091 B2 | 1/2010 | Olson et al. | |
| 7,665,646 B2 | 2/2010 | Prommersberger | |
| 7,708,759 B2 | 5/2010 | Lubbers et al. | |
| 7,727,246 B2 | 6/2010 | Sixto, Jr. et al. | |
| 7,727,248 B2 | 6/2010 | Smith et al. | |
| 7,731,718 B2 | 6/2010 | Schwammberger et al. | |
| 7,771,468 B2 | 8/2010 | Whitbourne et al. | |
| 7,794,484 B2 | 9/2010 | Stone et al. | |
| 7,819,896 B2 | 10/2010 | Racenet | |
| 7,824,426 B2 | 11/2010 | Racenet et al. | |
| 7,828,189 B2 | 11/2010 | Holsten et al. | |
| 7,842,097 B2 | 11/2010 | Yamamoto et al. | |
| 7,845,533 B2 | 12/2010 | Marczyk et al. | |
| 7,861,907 B2 | 1/2011 | Green et al. | |
| 7,887,551 B2 | 2/2011 | Bojarski et al. | |
| 7,891,531 B1 | 2/2011 | Ward | |
| 7,909,224 B2 | 3/2011 | Prommersberger | |
| 7,926,692 B2 | 4/2011 | Racenet et al. | |
| 7,942,304 B2 | 5/2011 | Taylor et al. | |
| 7,942,885 B2 | 5/2011 | Sixto, Jr. et al. | |
| 7,950,561 B2 | 5/2011 | Aranyi | |
| 3,006,700 A1 | 8/2011 | Demopulos et al. | |
| 3,008,598 A1 | 8/2011 | Whitman et al. | |
| 3,016,177 A1 | 9/2011 | Bettuchi et al. | |
| 3,016,178 A1 | 9/2011 | Olson et al. | |
| 3,021,378 A1 | 9/2011 | Sixto, Jr. et al. | |
| 8,011,550 B2 | 9/2011 | Aranyi et al. | |
| 8,029,563 B2 | 10/2011 | House et al. | |
| 8,033,439 B2 | 10/2011 | Racenet et al. | |
| 8,038,045 B2 | 10/2011 | Bettuchi et al. | |
| 8,043,328 B2 | 10/2011 | Hahnen et al. | |
| 8,057,524 B2 | 11/2011 | Meridew | |
| 8,062,314 B2 | 11/2011 | Sixto, Jr. et al. | |
| 8,062,330 B2 | 11/2011 | Prommersberger et al. | |
| 8,062,363 B2 | 11/2011 | Hirpara et al. | |
| 8,066,721 B2 | 11/2011 | Kortenbach et al. | |
| 8,070,033 B2 | 12/2011 | Milliman et al. | |
| 8,083,118 B2 | 12/2011 | Milliman et al. | |
| 8,083,119 B2 | 12/2011 | Prommersberger | |
| 8,083,120 B2 | 12/2011 | Shelton, IV et al. | |
| 8,087,563 B2 | 1/2012 | Milliman | |
| 8,113,409 B2 | 2/2012 | Cohen et al. | |
| 8,114,129 B2 | 2/2012 | Lubbers et al. | |
| 8,118,834 B1 | 2/2012 | Goraltchouk et al. | |
| 8,123,101 B2 | 2/2012 | Racen et al. | |
| 8,141,762 B2 | 3/2012 | Bedi et al. | |
| 8,157,151 B2 | 4/2012 | Ingmanson et al. | |
| 8,186,557 B2 | 5/2012 | Cohen et al. | |
| 8,186,560 B2 | 5/2012 | Hess et al. | |
| 8,205,620 B2 | 6/2012 | Taylor et al. | |
| 8,210,414 B2 | 7/2012 | Bettuchi et al. | |
| 8,210,416 B2 | 7/2012 | Milliman et al. | |
| 8,256,654 B2 | 9/2012 | Bettuchi et al. | |
| 8,256,656 B2 | 9/2012 | Milliman et al. | |
| 8,292,152 B2 | 10/2012 | Milliman et al. | |
| 8,298,286 B2 | 10/2012 | Trieu | |
| 8,308,041 B2 | 11/2012 | Kostrzewski | |
| 8,308,042 B2 | 11/2012 | Aranyi | |
| 8,308,046 B2 | 11/2012 | Prommersberger | |
| 8,322,455 B2 | 12/2012 | Shelton, IV et al. | |
| 8,328,061 B2 | 12/2012 | Kasvikis | |
| 8,342,377 B2 | 1/2013 | Milliman et al. | |
| 8,343,186 B2 | 1/2013 | Dreyfuss et al. | |
| 8,348,129 B2 | 1/2013 | Bedi et al. | |
| 8,439,936 B2 | 5/2013 | McClellan | |
| 8,453,905 B2 | 6/2013 | Holcomb et al. | |
| 8,453,910 B2 | 6/2013 | Bettuchi et al. | |
| 8,464,925 B2 | 6/2013 | Hull et al. | |
| 8,469,252 B2 | 6/2013 | Holcomb et al. | |
| 8,480,692 B2 | 7/2013 | McClellan | |
| 8,485,412 B2 | 7/2013 | Shelton, IV et al. | |
| 8,491,600 B2 | 7/2013 | McDevitt et al. | |
| 8,500,776 B2 | 8/2013 | Ebner | |
| 8,518,091 B2 | 8/2013 | McDevitt et al. | |

(56) References Cited

U.S. PATENT DOCUMENTS

| | | |
|---|---|---|
| 8,540,131 B2 | 9/2013 | Swayze |
| 8,550,325 B2 | 10/2013 | Cohen et al. |
| 8,574,275 B2 | 11/2013 | Stone et al. |
| 8,585,721 B2 | 11/2013 | Kirsch |
| 8,602,286 B2 | 12/2013 | Crainich et al. |
| 8,608,765 B1 | 12/2013 | Jurbala |
| 8,613,384 B2 | 12/2013 | Pastorelli et al. |
| 8,616,430 B2 | 12/2013 | (Prommersberger) Stopek |
| 8,623,052 B2 | 1/2014 | Dreyfuss et al. |
| 8,636,766 B2 | 1/2014 | Milliman et al. |
| 8,668,130 B2 | 3/2014 | Hess et al. |
| 8,684,249 B2 | 4/2014 | Racenet et al. |
| 8,720,766 B2 | 5/2014 | Hess et al. |
| 8,740,034 B2 | 6/2014 | Morgan et al. |
| 8,801,732 B2 | 8/2014 | Harris et al. |
| 8,801,755 B2 | 8/2014 | Dreyfuss et al. |
| 8,814,904 B2 | 8/2014 | Bennett |
| 8,834,543 B2 | 9/2014 | McDevitt et al. |
| 8,840,003 B2 | 9/2014 | Morgan et al. |
| 8,845,686 B2 | 9/2014 | Bennett |
| 8,905,287 B2 | 12/2014 | Racenet et al. |
| 8,939,983 B2 | 1/2015 | Stone et al. |
| 9,204,960 B2 | 12/2015 | Albertorio et al. |
| 9,277,909 B2 | 3/2016 | Brunsvold |
| 9,307,979 B1 | 4/2016 | Bennett et al. |
| 9,427,309 B2 | 8/2016 | Kubiak et al. |
| 9,439,645 B2 | 9/2016 | Stone et al. |
| 9,451,961 B2 | 9/2016 | Kubiak |
| 9,486,207 B2 | 11/2016 | Dooney, Jr. et al. |
| 9,642,610 B2 | 5/2017 | Albertorio et al. |
| 9,655,625 B2 | 5/2017 | Kubiak et al. |
| 9,700,305 B2 | 7/2017 | Bennett et al. |
| 10,219,804 B2 | 3/2019 | Linder et al. |
| 10,299,842 B2* | 5/2019 | Hollis ............... A61B 17/84 |
| 10,835,241 B2 | 11/2020 | Kubiak et al. |
| 2001/0044637 A1 | 11/2001 | Jacobs et al. |
| 2001/0051815 A1 | 12/2001 | Esplin |
| 2002/0013298 A1 | 1/2002 | Hunter |
| 2002/0022861 A1 | 2/2002 | Jacobs et al. |
| 2002/0055666 A1 | 5/2002 | Hunter et al. |
| 2002/0077661 A1 | 6/2002 | Saadat |
| 2002/0123750 A1 | 9/2002 | Eisermann et al. |
| 2002/0173807 A1* | 11/2002 | Jacobs ............... A61B 17/11 606/151 |
| 2002/0192280 A1 | 12/2002 | Hunter et al. |
| 2003/0065360 A1* | 4/2003 | Jacobs ............... A61B 17/11 606/216 |
| 2003/0069602 A1 | 4/2003 | Jacobs et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130735 A1* | 7/2003 | Rogalski ............ A61F 2/0811 623/13.15 |
| 2003/0153972 A1 | 8/2003 | Helmus |
| 2003/0157170 A1 | 8/2003 | Liggins et al. |
| 2003/0181371 A1 | 9/2003 | Hunter et al. |
| 2003/0203976 A1 | 10/2003 | Hunter et al. |
| 2004/0006352 A1 | 1/2004 | Nobles et al. |
| 2004/0010276 A1 | 1/2004 | Jacobs et al. |
| 2004/0039404 A1 | 2/2004 | Dreyfuss |
| 2004/0059336 A1 | 3/2004 | Lombardo et al. |
| 2004/0060410 A1 | 4/2004 | Leung et al. |
| 2004/0076672 A1 | 4/2004 | Hunter et al. |
| 2004/0088003 A1 | 5/2004 | Leung et al. |
| 2004/0153153 A1 | 8/2004 | Elson et al. |
| 2004/0193217 A1 | 9/2004 | Lubbers et al. |
| 2004/0199241 A1 | 10/2004 | Gravett et al. |
| 2004/0219214 A1 | 11/2004 | Gravett et al. |
| 2004/0220591 A1 | 11/2004 | Bonutti |
| 2004/0220616 A1* | 11/2004 | Bonutti ............. A61B 17/0487 606/232 |
| 2004/0224023 A1 | 11/2004 | Hunter et al. |
| 2004/0254609 A1 | 12/2004 | Esplin |
| 2004/0260340 A1* | 12/2004 | Jacobs ............... A61B 17/08 606/213 |
| 2004/0267362 A1 | 12/2004 | Hwang et al. |
| 2005/0090827 A1 | 4/2005 | Gedebou |
| 2005/0152941 A1 | 7/2005 | Hunter et al. |
| 2005/0175665 A1 | 8/2005 | Hunter et al. |
| 2005/0186261 A1 | 8/2005 | Avelar et al. |
| 2005/0192428 A1 | 9/2005 | Berg et al. |
| 2005/0197699 A1 | 9/2005 | Jacobs et al. |
| 2006/0127445 A1 | 6/2006 | Hunter et al. |
| 2006/0135994 A1 | 6/2006 | Ruff et al. |
| 2006/0147332 A1 | 7/2006 | Jones |
| 2006/0149349 A1 | 7/2006 | Garbe |
| 2006/0240064 A9 | 10/2006 | Hunter et al. |
| 2006/0240113 A1 | 10/2006 | Hunter et al. |
| 2006/0247641 A1 | 11/2006 | Re et al. |
| 2007/0021779 A1 | 1/2007 | Garvin et al. |
| 2007/0026043 A1 | 2/2007 | Guan et al. |
| 2007/0027527 A1 | 2/2007 | Williams et al. |
| 2007/0065663 A1 | 3/2007 | Trull et al. |
| 2007/0123984 A1 | 5/2007 | Hodorek |
| 2007/0156158 A1 | 7/2007 | Herzberg et al. |
| 2007/0162022 A1* | 7/2007 | Zhang ............... A61F 2/0811 606/323 |
| 2007/0196421 A1 | 8/2007 | Hunter et al. |
| 2007/0208355 A1 | 9/2007 | Ruff |
| 2007/0208377 A1 | 9/2007 | Kaplan et al. |
| 2008/0003394 A1 | 1/2008 | Eke |
| 2008/0027443 A1 | 1/2008 | Lambert |
| 2008/0027445 A1 | 1/2008 | Brown, Jr. et al. |
| 2008/0027446 A1 | 1/2008 | Stone et al. |
| 2008/0027486 A1 | 1/2008 | Jones et al. |
| 2008/0051888 A1 | 2/2008 | Ratcliffe et al. |
| 2008/0058579 A1 | 3/2008 | Hunter et al. |
| 2008/0124400 A1 | 5/2008 | Liggins et al. |
| 2008/0195204 A1 | 8/2008 | Zhukauskas et al. |
| 2008/0234731 A1 | 9/2008 | Leung et al. |
| 2008/0247987 A1 | 10/2008 | Liggins et al. |
| 2008/0281325 A1 | 11/2008 | Stone et al. |
| 2008/0312315 A1 | 12/2008 | Daniloff et al. |
| 2009/0012560 A1 | 1/2009 | Hunter et al. |
| 2009/0018577 A1 | 1/2009 | Leung et al. |
| 2009/0020584 A1 | 1/2009 | Soltz et al. |
| 2009/0048537 A1 | 2/2009 | Lydon et al. |
| 2009/0048616 A1 | 2/2009 | Gonzalez-Hernandez |
| 2009/0060973 A1 | 3/2009 | Hunter et al. |
| 2009/0107965 A1 | 4/2009 | D'Agostino |
| 2009/0112259 A1 | 4/2009 | D'Agostino |
| 2009/0117070 A1 | 5/2009 | Daniloff et al. |
| 2009/0125094 A1 | 5/2009 | Rust |
| 2009/0143819 A1 | 6/2009 | D'Agostino |
| 2009/0149884 A1 | 6/2009 | Snyder et al. |
| 2009/0156980 A1 | 6/2009 | Eaton et al. |
| 2009/0216326 A1 | 8/2009 | Hirpara et al. |
| 2009/0222039 A1 | 9/2009 | Dreyfuss et al. |
| 2009/0226500 A1 | 9/2009 | Avelar et al. |
| 2009/0228021 A1 | 9/2009 | Leung |
| 2009/0234386 A1 | 9/2009 | Dean et al. |
| 2009/0280153 A1 | 11/2009 | Hunter et al. |
| 2009/0324720 A1 | 12/2009 | He et al. |
| 2010/0016872 A1 | 1/2010 | Bayton et al. |
| 2010/0023052 A1 | 1/2010 | Heinrich et al. |
| 2010/0160718 A1 | 6/2010 | Villafana et al. |
| 2010/0193568 A1 | 8/2010 | Scheib et al. |
| 2010/0217314 A1 | 8/2010 | Holsten et al. |
| 2010/0228078 A1* | 9/2010 | Safer ............... A61B 17/0401 600/30 |
| 2010/0249802 A1 | 9/2010 | May et al. |
| 2010/0324676 A1 | 12/2010 | Albertorio et al. |
| 2011/0106253 A1 | 5/2011 | Barwood et al. |
| 2011/0124956 A1 | 5/2011 | Mujwid |
| 2011/0125287 A1 | 5/2011 | Hotter et al. |
| 2011/0155787 A1 | 6/2011 | Baxter, III et al. |
| 2011/0288565 A1 | 11/2011 | Kubiak et al. |
| 2011/0288566 A1 | 11/2011 | Kubiak |
| 2011/0301706 A1 | 12/2011 | Brooks et al. |
| 2012/0080336 A1 | 4/2012 | Shelton, IV et al. |
| 2012/0130374 A1 | 5/2012 | Bouduban et al. |
| 2012/0203253 A1 | 8/2012 | Kubiak |

(56) References Cited

U.S. PATENT DOCUMENTS

| | | | |
|---|---|---|---|
| 2012/0245629 | A1 | 9/2012 | Gross et al. |
| 2013/0131781 | A1 | 5/2013 | Greenhalgh et al. |
| 2013/0144310 | A1 | 6/2013 | Gordon et al. |
| 2013/0197580 | A1 | 8/2013 | Perriello et al. |
| 2014/0039551 | A1 | 2/2014 | Donahue |
| 2014/0067061 | A1* | 3/2014 | Kubiak ............. A61B 17/064 623/13.14 |
| 2014/0214037 | A1 | 7/2014 | Mayer et al. |
| 2015/0245841 | A1 | 9/2015 | Linder et al. |
| 2015/0272567 | A1 | 10/2015 | Feezor et al. |
| 2015/0289866 | A1 | 10/2015 | Bowen et al. |
| 2016/0066900 | A1 | 3/2016 | Brunsvold et al. |
| 2016/0066907 | A1* | 3/2016 | Cheney ............. A61B 17/0642 606/75 |
| 2016/0100835 | A1 | 4/2016 | Linder et al. |
| 2016/0100933 | A1 | 4/2016 | Linder et al. |
| 2016/0174965 | A1 | 6/2016 | Brunsvold |
| 2017/0027578 | A1 | 2/2017 | Friedman et al. |
| 2017/0056158 | A1 | 3/2017 | Saing |
| 2017/0156847 | A1 | 6/2017 | Ricci et al. |
| 2017/0333026 | A1 | 11/2017 | Dreyfuss et al. |
| 2018/0078253 | A1 | 3/2018 | Kubiak et al. |
| 2018/0200042 | A1 | 7/2018 | Kubiak et al. |

OTHER PUBLICATIONS

Momose et al., "Suture Techniques With High Breaking Strength And Low Gliding Resistance: Experiments In The Dog Flexor Digitorum Pofundus Tendon," Acta Orthop Scand, 2001, 72(6):635-641.

Leung et al., "Barbed, Bi-Directional Medical Sutures: Biomechanical Properties And Wound Closure Efficacy Study," Society for Biomaterials 28ths Annual Meeting Transactions, 2002, p. 724.

Chunfeng et al., "Enhancing The Strength Of The Tendon-Suture Interface Using 1-Ethyl-3-(3-dimethylaminoproply) Carbodimide Hydrochloride And Cyanoacrylate," Journal of Hand Surger, 2007, 32(5): 606-11.

Burkhead et al., "Use Of Graft Jacket As An Augmentation For Massive Rotator Cuff Tears," Semin Arthro, 2007, 18(1): 11-18.

Hirpara et al., "A Barbed Device For Digital Flexor Tendon Repair," http://proceedings.jbjs.org.uk/cgi/content/abstract/92-B/SUPP_II/291-d, Mar. 2010.

Office Action with English Translation issued in CN 201580066314.4 dated Jun. 22, 2018.

Supplementary European Search Report issued in EP 15850646.9 dated Jun. 25, 2018.

International Search Report dated Feb. 26, 2016 for International Application No. PCT/US2015/56059 (14 pages).

International Search Report dated Jul. 20, 2015 for International Application No. PCT/US2015/020231 (10 pages).

International Search Report dated Oct. 10, 2013 for International Application No. PCT/US2013/052735 (7 pages).

International Search Report dated May 8, 2019 for International Application No. PCT/US2019/018628 (14 pages).

Office Action issued in EP 15850646.9 dated Sep. 19, 2019.

Supplementary European Search Report dated Oct. 20, 2021 for European App. No. 19/756,761 (10 pages).

* cited by examiner

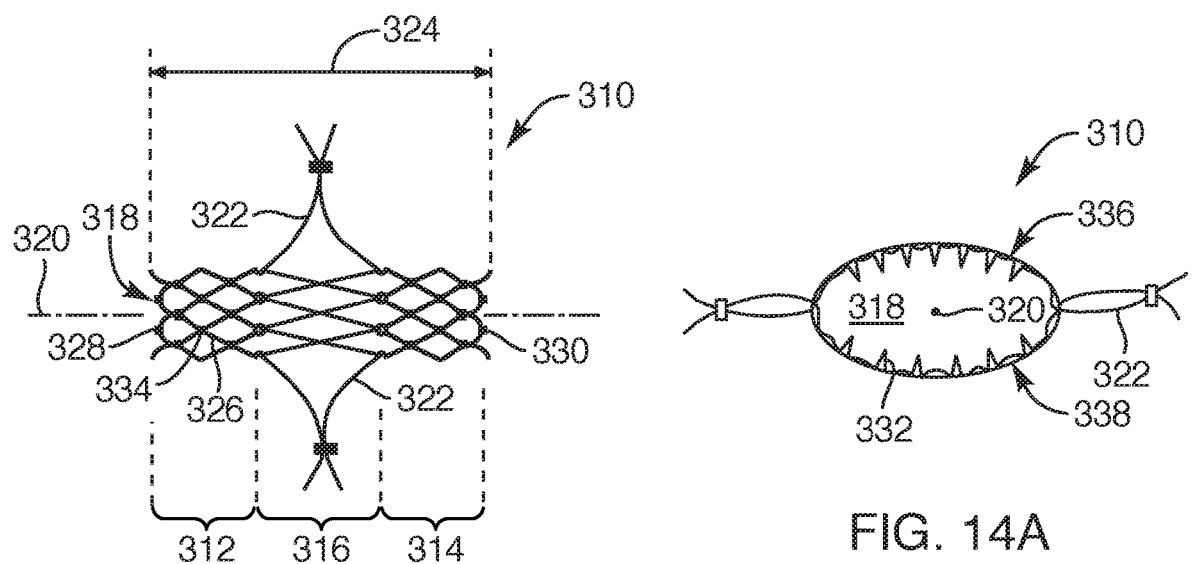
FIG. 14
FIG. 14A
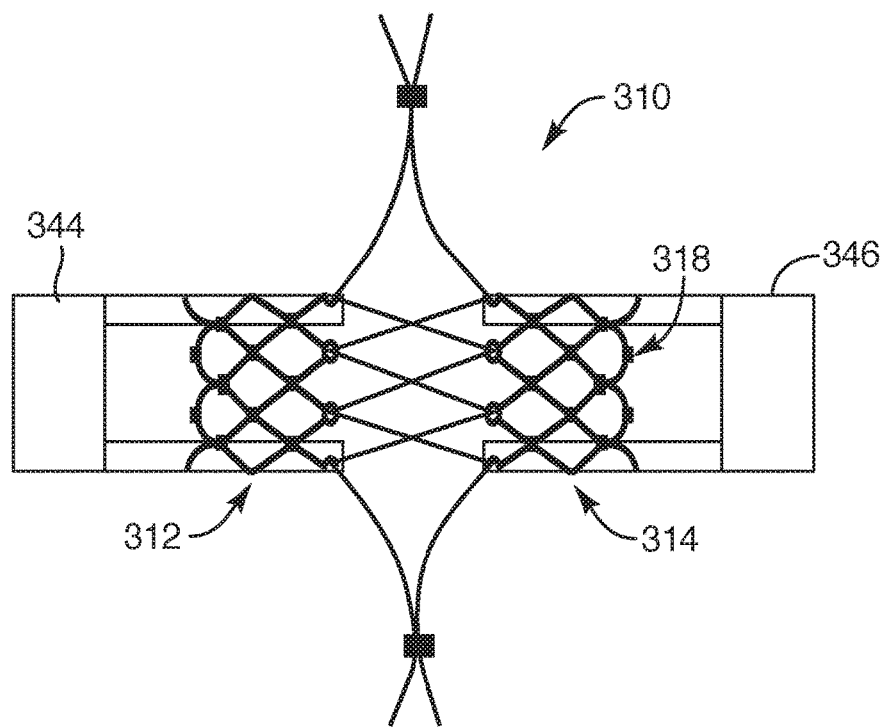
FIG. 15

SOFT TISSUE TO BONE REPAIR DEVICES, SYSTEMS, AND METHODS

CROSS-REFERENCE TO RELATED APPLICATIONS

The present application is a continuation of U.S. application Ser. No. 14/885,956, filed Oct. 16, 2015, which claims the benefit of U.S. Provisional Application No. 62/064,533, filed Oct. 16, 2014, the disclosures of which are hereby incorporated by reference herein in their entirety. Further, U.S. application Ser. No. 14/885,956 is also a continuation-in-part of U.S. application Ser. No. 13/953,709, filed Jul. 29, 2013, now U.S. Pat. No. 9,427,309, which claims the benefit of U.S. Provisional Application No. 61/677,239, filed on Jul. 30, 2012, and U.S. Provisional Application No. 61/804,570, filed on Mar. 22, 2013, the disclosures of which are hereby incorporated by reference herein in their entirety.

TECHNICAL FIELD

The present invention relates generally to soft tissue repair. More particularly, the present invention relates to devices, systems, and methods for fixating soft tissue to bone.

BACKGROUND

Lacerated flexor tendon repair, as an example, is a procedure performed approximately 145,000 times a year in the United States alone. For all types of tendons in the human anatomy, early post-operative mobilization is beneficial to restoring maximal tendon function following injury and repair. Adhesion formation is a common complication following tendon repair, but can be reduced through motion rehabilitation programs. By preventing adhesion formation and gliding resistance, tendon healing may be enhanced. However, the failure rate of tendon repairs is close to 30 percent, primarily because of overloading at the repair site. Although an objective of tendon repair is to provide adequate strength for passive and active motion during rehabilitation, it is important to maintain a delicate balance between rehabilitative motion protocols and fatiguing the repair site.

A procedure for lacerated tendon repair is to use suture to mend the two ends of a tendon together using complex suture patterns. While this provides a good initial repair, the strength and quality of the repair may quickly degrade with subsequent loading and mobilization. Although postoperative therapy may be utilized to reduce adhesion, the resulting tension can induce gap formation or tendon rupture at the repair site, seriously impairing the outcome of the repair. Gapping at the repair site has many negative effects, such as reduced repair strength, tendon rupture, and an increased probability for adhesion. Further, complex suture patterns are also used for fixating soft tissue to bone, resulting in similar negative effects to the patient and often result in subsequent procedures depending on the activity level of the patient. Furthermore, such complex suturing procedures are time consuming and typically require specialized surgeons to perform such procedures.

BRIEF SUMMARY OF THE INVENTION

Embodiments of the present invention are directed to various devices, systems and methods for fixating soft tissue to bone. For example, in one embodiment, a repair device system for fixating soft tissue to bone is provided. The repair device system includes a carrier member, multiple anchors, and a bone anchor. The carrier member includes multiple pad portions and a bone coupling portion, each of the pad portions being aligned with an adjacent pad portion and each of the pad portions having at least one opening defined therein. The pad portions are configured to be positioned over a side of the soft tissue. The bone coupling portion is coupled to the multiple pad portions. Each anchor is sized and configured to extend through the at least one opening defined in one of the multiple pad portions and through the soft tissue. With this arrangement, the bone anchor is configured to be coupled to the bone coupling portion and configured to be secured to the bone.

In one embodiment, the multiple anchors comprise a u-shaped configuration. In another embodiment, the multiple anchors are separate and discrete relative to the carrier member.

In another embodiment, the carrier member is a monolithic structure. In another embodiment, the multiple pad portions are interconnected with rigid struts. In still another embodiment, the pad portions are interconnected with at least one filament.

In another embodiment, the multiple pad portions include opposing pad portions configured to be positioned over opposing sides of the soft tissue such that one of the multiple anchors extends through at least one opening defined in each of the opposing pad portions to sandwich the soft tissue between the opposing pad portions. In a further embodiment, the opposing pad portions are interconnected with struts extending therebetween.

In accordance with another embodiment of the present invention, a repair device system for fixating soft tissue to bone is provided. The repair device system includes a carrier member, multiple anchors, and a bone coupling portion. The carrier member includes first pad portions and second pad portions, the first pad portions being positioned opposite the second pad portions. As such, the first pad portions are configured to be positioned on a first side of the soft tissue and the second pad portions are configured to be positioned on an opposite, second side of the soft tissue. Each anchor is sized and configured to extend over one of the first pad portions, extend through the soft tissue, and extend to wrap over a portion of one of the second pad portions. The bone coupling portion is coupled to at least one of the first and second pad portions.

In one embodiment, the repair device system further includes a bone anchor configured to be coupled to the bone coupling portion. In another embodiment, the first and second pad portions each include three oppositely positioned pad portions. In another embodiment, the carrier member is a monolithic structure. In still another embodiment, the first pad portions are interconnected to the second pad portions. In another embodiment, the first pad portions are separate and discrete relative to the second pad portions, the first pad portions being configured to be coupled to the second pad portions with the multiple anchors.

In another embodiment, the multiple anchors include a u-shaped configuration. In another embodiment, the multiple anchors are separate and discrete structures relative to the carrier member.

In accordance with another embodiment of the present invention, a method of fixating soft tissue to bone is provided. The method steps includes positioning a carrier member with multiple pad portions and a bone coupling portion such that the multiple pad portions are positioned adjacent a portion of the soft tissue; anchoring the carrier member to the soft tissue by inserting anchors along at least one opening defined in the multiple pad portions such that the anchors extend through the soft tissue and fixate the carrier member to the soft tissue; coupling a bone anchor to the bone coupling portion; and securing the bone anchor to the bone.

In one embodiment, the method step of positioning includes positioning the carrier member with first pad portions and second pad portions of the multiple pad portions such that the first pad portions and the second pad portions are positioned on opposite sides of the soft tissue. In another embodiment, the method step of anchoring includes securing the soft tissue to the carrier by deploying each of the anchors to extend over one of the first pad portions, to extend through the soft tissue, and extend to wrap over a portion of one of the second pad portions.

BRIEF DESCRIPTION OF THE SEVERAL
VIEWS OF THE DRAWINGS

The foregoing and other advantages of the invention will become apparent upon reading the following detailed description and upon reference to the drawings in which:

FIG. 14 is a top view of another embodiment of a repair device, according to the present invention;

FIG. 14A is a side view of the repair device of FIG. 14, according to another embodiment of the present invention;

FIG. 15 is a top view of the repair device, depicting first and second applicators inserted into opposite ends of the repair device, according to another embodiment of the present invention;

DETAILED DESCRIPTION OF THE INVENTION

Figure 1:
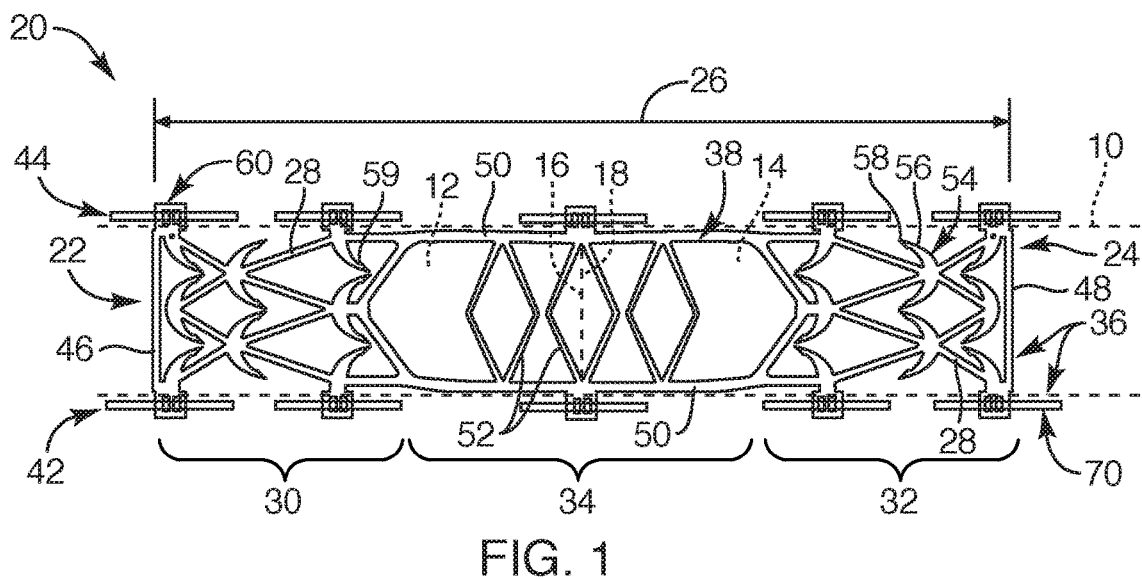
FIG. 1 is a top view of a repair device, depicting a tendon positioned within the repair device, according to an embodiment of the present invention.
Figure 2:
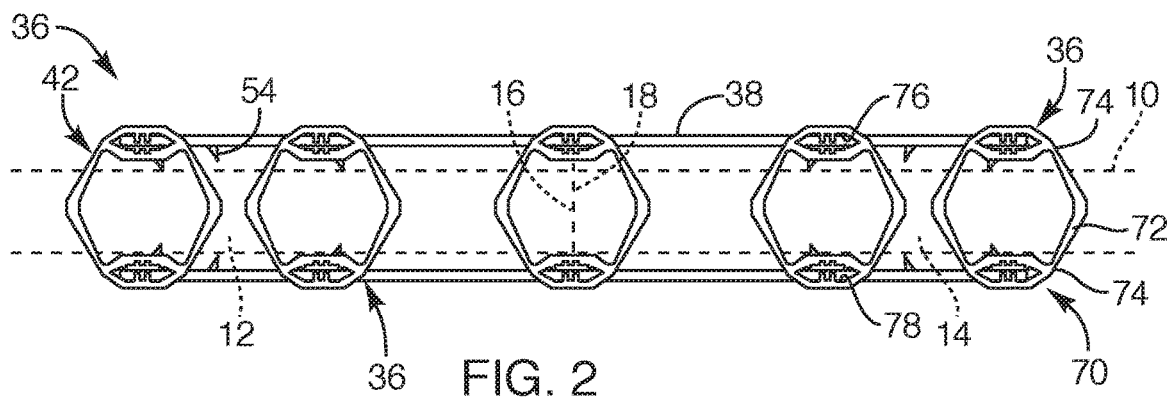
FIG. 2 is a side view of the repair device shown in FIG. 1, according the present invention.
Figure 3:
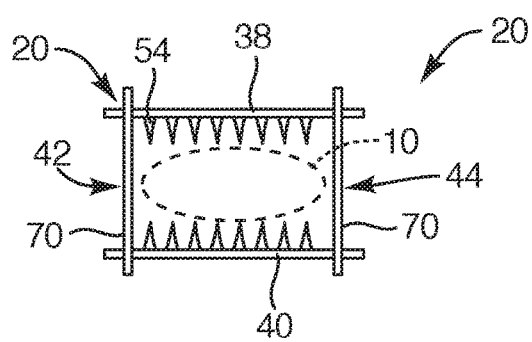
FIG. 3 is an end view of the repair device shown in FIG. 1, depicting the device in a non-engaging first position relative to the tendon, according to one embodiment of the present invention.
Figure 4:
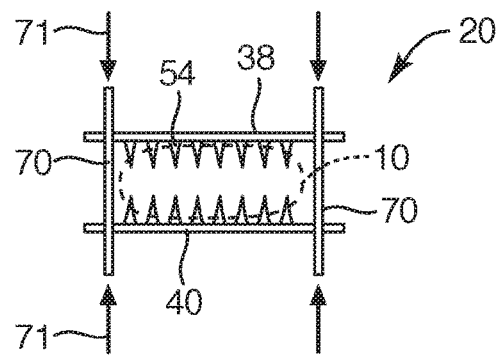
FIG. 4 is an end view of the repair device, depicting the device in an engaging second position relative to the tendon, according to another embodiment of the present invention.

Referring to FIGS. 1-3, a soft tissue repair device 20 is depicted. Such a repair device 20 may be sized and configured to approximate and fuse, for example, a lacerated tendon 10 together. The tendon 10, shown in outline form, may be positioned in the repair device 20 such that a first tendon portion 12 and a second tendon portion 14 with respective first and second tendon ends 16, 18 are abutted against each other. The repair device 20 may include a tubular configuration with opposing first and second open ends 22, 24 to facilitate insertion of the first and second tendon portions 12, 14 therein such that the first and second tendon ends 16, 18 are positioned at about a mid-point of the repair device 20. The repair device 20 may then be moved from a first, non-engaging position to a second, engaging position (FIG. 4).

The repair device 20 may be elongated with a longitudinal length 26 to exhibit the tubular configuration formed from multiple interconnecting struts 28 to define a multi-cellular structure. The struts 28 of the repair device 20 may include structural characteristics that facilitate and resist elongation along portions of the length 26 of the repair device 20. For example, the repair device 20 may include a first portion 30 and a second portion 32 with an intermediate portion 34 therebetween, each extending along the longitudinal length 28 of the repair device 20. The intermediate portion 34 may be configured to substantially resist elongation so that the first and second tendon ends 16, 18 positioned adjacent the intermediate portion 34 maintain their abutted relationship. The first and second portions 30, 32 of the repair device 20 may be configured to engage the tendon 10 and elongate as the tendon elongates to facilitate functionality and a load placed upon the tendon 10. Such elongation of the first and second portions 30, 32 and resistance to elongate at the intermediate portion 34 also substantially prevents overloading and, thus, gapping of the tendon 10 at the repair site.

The repair device 20 may include a frame structure 36. The frame structure 36 may include an upper frame portion 38, a lower frame portion 40, a first side portion 42, and a second side portion 44, each of which portions may be coupled together to form the tubular configuration with a cross-section having a square or rectangular configuration. The upper frame portion 38 and the lower frame portion 40 may be substantially similar in structure as well as the first and second side portions 42, 44 may be substantially similar in structure. Further, the upper frame portion 38 and the lower frame portion 40 may be formed from a variety of metallic materials, such as stainless steel or various alloys, but preferably a super elastic material, such as Nitinol, to provide the desired structural strain characteristics. The first and second side portions 42, 44 may also be formed from a metallic material, such as stainless steel or Nitinol, or both, discussed hereafter.

With reference to FIG. 1, structural features and characteristics will now be set froth for the upper frame portion 38, which will apply equally to the lower frame portion 40. The upper frame portion 38, similar to the lower frame portion (not shown), may include the before-described first portion 30 and the second portion 32 with the intermediate portion 34 therebetween each extending along the longitudinal length 26 of the upper frame portion 38. The first portion 30 extends along the longitudinal length 26 between the intermediate portion 34 and a first end 46 of the upper frame portion. Likewise, the second portion 32 extends along the longitudinal length 26 between the intermediate portion 34 and a second end 48 of the upper frame portion 38. The intermediate portion 34 may be defined by outer rails 50 extending substantially parallel to each other with intermediate stoppers 52 extending laterally between the outer rails 50. The stoppers 52 may be in the form of laterally extending struts between the outer rails 50.

As previously set forth, the repair device 20 includes multiple interconnecting struts 28 defining a multi-cellular structure. For example, the struts 28 of the first portion 30 and the second portion 32 may extend, for the most part, at various angles relative to the longitudinal length 26 of the upper frame portion 38. Such struts 28 of the first portion 30 and the second portion 32 may be sized and configured to facilitate elongation of the respective first and second portions 30, 32 of the upper frame portion 38 such that the struts 28 may flex. In one embodiment, the elongation of the first and second portions 30, 32 of the upper frame portion 38 may gradually increase toward the first and second ends 46, 48 of the upper frame portion 38, respectively. In another embodiment, the strainability or elongation of the first and second portion 30, 32 may increase toward their respective ends in a gradient type manner. The struts 28 of the first and second portions 30, 32 of the upper frame portion 38 may include a substantially constant width along their respective longitudinal strut lengths. In another embodiment, the struts 28 may include a tapered portion along the longitudinal strut lengths to facilitate elongation along the length 26 of the first and second portions 30, 32 of the upper frame portion 38. In still another embodiment, the struts 26 may include a radius along their respective length having a constant width or a taper to facilitate elongation of the first portion 30 and the second portion 32.

The intermediate portion 34 of the upper frame portion 38 may include struts 28 sized and oriented to substantially prevent elongation along the length of the intermediate portion 34. For example, the struts or the rails along the length of the intermediate portion 34, being substantially parallel, substantially limit the ability of the intermediate portion 34 to elongate. As known to one of ordinary skill in the art, other structural features and characteristics may be employed to substantially limit elongation of the intermediate portion 34 as well. The intermediate stoppers 52 may be sized and configured to substantially prevent trumpeting of the first and second tendon ends 16, 18, or tendon portions adjacent thereto, from extending beyond or outside of a plane of the upper and lower frame portions 38, 40.

With respect to FIGS. 1 and 3, the first and second portions 30, 32 of the upper and lower frame portions 38, 40 may include tines 54. In another embodiment, the intermediate portion 34 may also include tines 54. The tines 54 may be sized and configured to aggressively engage and grab the tendon 10 without damaging the tendon. The tines 54 may include a radius and a tapered portion 56 extending to a point 58. The tines 54 may extend from an end portion of a given strut 28 or a node or juncture between adjacently extending struts 28, the tines 54 extending from the first and second portions 30, 32 of the frame structure 36. The tines 54 of the upper frame portion 38 may extend with an orientation toward the intermediate portion 34 and downward. The tines 54 of the lower frame portion 40 may extend with an orientation toward the intermediate portion 34 and upward. Such orientation may be at an acute angle (see FIG. 2) relative to the planes of the respective upper and lower frame portions 38, 40. Such orientation facilitates ready insertion into the tubular configuration of the repair device 20 as well as enhances grabbing the tendon to prevent migration therefrom once the repair device 20 is moved to the second engaging position (FIG. 4). Further, the tines 54 may be configured to flex slightly so as to a grab the tissue but upon tension being placed on the tendon 10 the tines 54 may slightly move or bend to substantially prevent further damage to the tendon. In one embodiment, the tines 54 may extend substantially orthogonal relative to the plane of the respective upper and lower frame portions 38, 40. In another embodiment, the tines 54 may include one or more barbs 59.

Figure 5:
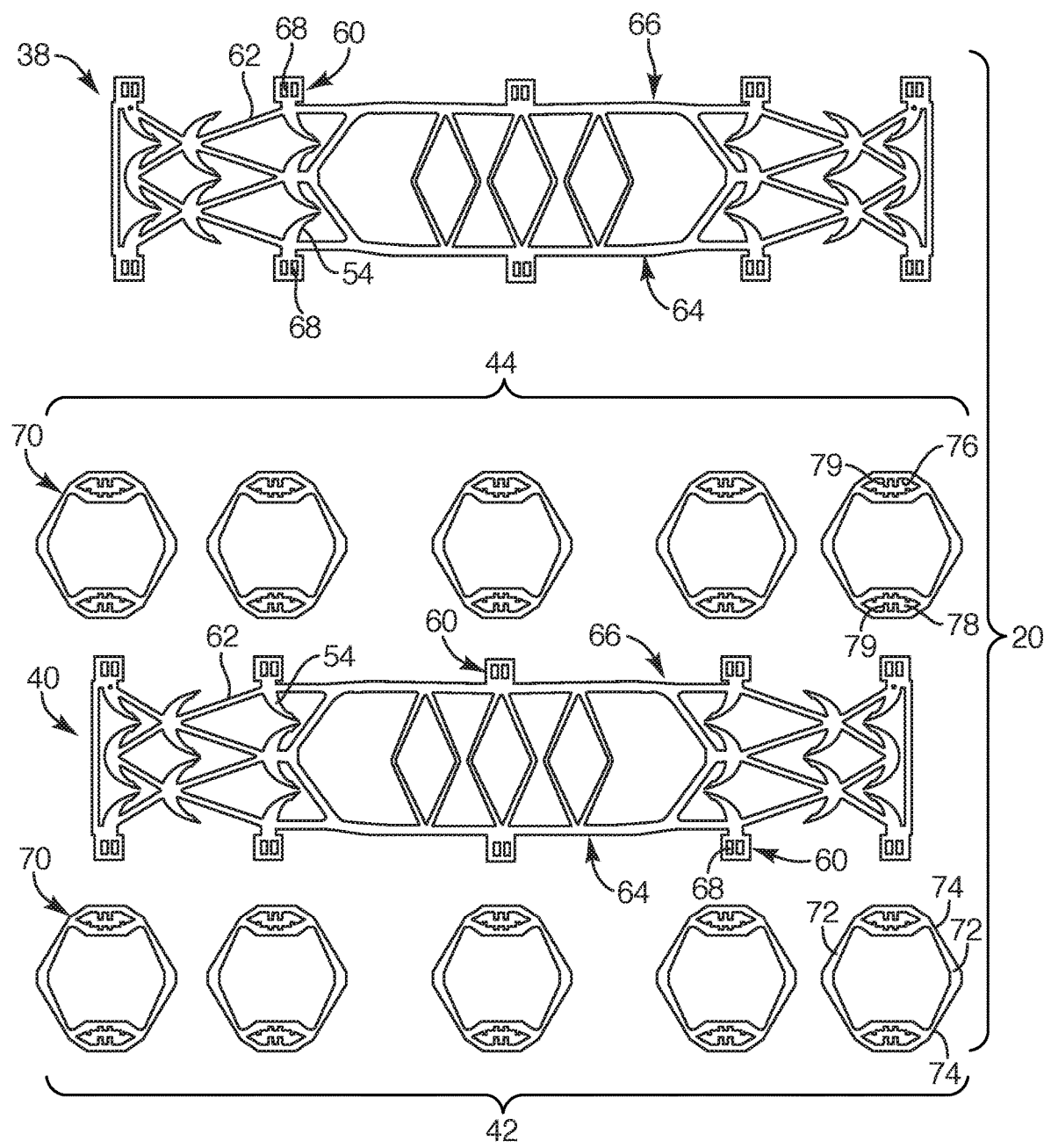
FIG. 5 is an unassembled view of the repair device shown in FIG. 1, depicting various components of a frame including an upper frame portion, a lower frame portion, and side crimps, according to an embodiment of the present invention.

With respect to FIGS. 1, 2 and 5, the upper frame portion 38 and the lower frame portion 40 may include tabs 60. The tabs 60 may extend at or from a periphery 62 of each of the upper and lower frame portions 38, 40. More particularly, the upper frame portion 38 includes a first side 64 and a second side 66 each with at least two tabs 60 (one for each end of the first and second sides 64, 66) and, in this embodiment, five tabs 60 for each of the first and second sides 64, 66. The tabs 60 on the first side 64 correspond and align with the tabs 60 on the second side 66. The tabs 60 for the upper frame portion 38 may correspond and align with the number of tabs 60 for the lower frame portion 40. Each tab 60 may include one or more openings 68 defined therein sized and configured to couple to a side crimp 70.

The first side portion 42 and the second side portion 44 of the repair device 20 may each include at least two side crimps 70 with one at each end to couple to the upper and lower frame portions 38, 40. In this embodiment, the first side portion 42 and the second side portion 44 each includes five side crimps 70. As previously set forth, the side crimps 70 may be sized and configured to couple to the upper and lower frame portions 38, 40. For example, each side crimp 70 may include a closed periphery with side arm portions 72 sized and configured to buckle under a defined force. The side arm portions 72 may include one or more weak portions 74 so as to facilitate the side crimps 70 to deform or buckle upon a force being placed thereto. The side crimps 70 may define an upper opening 76 and a lower opening 78 with structure, such as, teeth 79 that extend in the openings sized and configured to latch or couple to the tabs 60 of the upper and lower frame portions 38, 40, respectively. In other words, the teeth 79 defining a portion of the upper opening 76 of one side crimp 70 may be sized to couple to one of the tabs 60 of the upper frame portion 38. Likewise, the structure or teeth 79 defining a portion of the lower opening 78 of the one side crimp 70 may be sized to couple to one of the tabs 60 of the lower frame portion 40. With this arrangement, the side crimps 70 couple the upper and lower frame portions 38, 40 to provide a tubular configuration to serve as a cage or box-like structure to position the tendon 10 therethrough. The side crimps 70 may be formed from a metallic material, such as a stainless steel. In another embodiment, the side crimps may be formed from a super-elastic material, such as Nitinol.

The side crimps, as depicted in FIGS. 3 and 4, may serve to facilitate the repair device 20 in maintaining its position at both the first non-engaging position and the second engaging position. In particular, in an embodiment where the side crimps 70 are, for example, stainless steel or the like, the structural characteristics of the side crimps 70 maintain the upper and lower frame portions 38, 40 in the first non-engaging position so that the tendon 10 may be easily positioned within the repair device 20. Once the tendon 10 is appropriately positioned within the repair device 20, a force 71 may be placed upon the repair device 20 to sandwich the tendon 10 within the repair device 20 such that the tines 54 engage the tendon 10. Such force 71 buckles the side crimps 70 at the weak portions (not shown) defined therein to facilitate the upper frame portion 38 to move closer to the lower frame portion 40. Due to the structural characteristics of, for example, stainless steel, the side crimps 70 maintain their buckled position to, thereby, maintain the repair device 20 in the second engaging position.

In another embodiment, as previously set forth, the side crimps 70 or first and second side portions 42, 44 of the repair device 20 may be made from a super-elastic material. In such an embodiment, the first and second side portions 42, 44 (FIG. 1) may be constrained to an expanded position with, for example, applicators (see FIGS. 9B and 12) at each end to maintain the repair device in the first non-engaging position. Once the lacerated tendon 10 is inserted within the repair device 20, the applicators may be removed, after which, the first and second side portions 42, 44 may then move toward a relaxed state such that the repair device 20 moves to the second engaging position. In the second engaging position, the upper and lower frame portions 38, 40 move toward each other such that the tines 54 extending from the upper and lower frame portions 38, 40 engage the tendon 10.

In another embodiment, the first and second side portions 42, 44 (FIG. 1) may be formed with a super-elastic material and a stainless steel material or the like. In this embodiment, side crimps 70 may be employed at both ends of the first and second side portions 42, 44 of the repair device 20 with, for example, struts or crimps between the side crimps 70 at the ends. Such an embodiment may need the applicators to maintain the device 20 in the first non-engaging position. Once the applicators are removed, the super-elastic struts or crimps pull the upper and lower frame portions 38, 40 closer together. A force may then be applied to the ends of the first and second side portions 42, 44 to buckle the stainless steel side crimps 70 at the ends of the repair device 20.

Now referring to FIG. 5, one embodiment of an unassembled repair device 20 is shown. Each of the upper and lower frame portions 38, 40 and the side crimps 70 may be laser cut from a flat sheet of metallic material and, as such, the structural components are substantially flat and planar with a low profile (See FIG. 3). As previously set forth, the upper and lower frame portions 38, 40 may be formed from a super-elastic sheet material, such as Nitinol. The side crimps may be formed from a stainless steel sheet material and/or a super-elastic sheet material. As previously set forth, the tines 54 of the upper and lower frame portions 38, 40 may be oriented out-of-plane relative to the upper and lower frame portions 38, 40 from which they respectively extend. As known by one of skill in the art, such orientation may be employed by heat-setting the tines 54 to a pre-determined orientation. Once the heat setting of the tines 54 is completed, the repair device 20 may be assembled. For example, as set forth above, the lower opening 78 defined in each of the side crimps 70 may be coupled to the tabs 60 of the lower frame portion 40. The upper opening 76 defined in the side crimps 70 may then be coupled to the tabs 60 of the upper frame portion 38, as depicted in FIGS. 1 and 2, to thereby assemble the repair device 20.

Figure 5A:
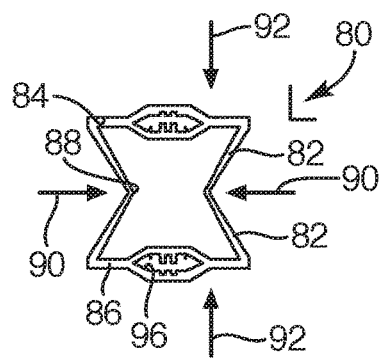
FIG. 5A is another embodiment of a side crimp, according to the present invention.

With respect to FIG. 5A, another embodiment of a side crimp 80 is depicted. In this embodiment, the side crimp 80 may include a closed periphery with arm portions 82 extending between an upper crimp portion 84 and a lower crimp portion 86. The arm portions 82 may include weak portions 88 to facilitate buckling of the side crimp 80, as indicated by arrow 90, upon a force 92 being applied to the side crimp 80. As in the previous side crimp embodiment, the side crimp 80 may include an upper opening 94 and a lower opening 96 defined in the upper crimp portion 84 and lower crimp portion 86, respectively, configured to couple to tabs 60 of the upper and lower frame portions 38, 40. As known by one of ordinary skill in the art, other structural configurations may be employed for the side crimps 80 to facilitate crimping the repair device 20 to the second engaging position.

Figure 6:
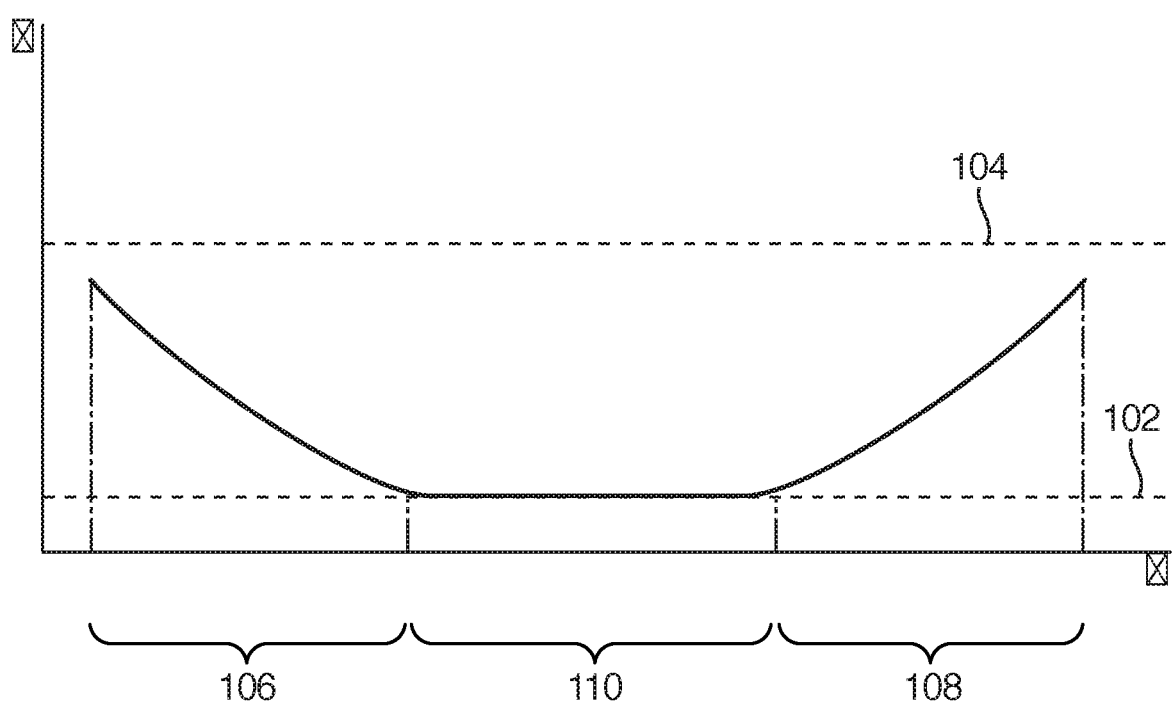
FIG. 6 is graph showing the strain along the length of the repair device, according to one embodiment of the present invention.

With respect to FIG. 6, a graph, strain € vs. length X, representing the strainability along the length of the repair device 20 under typical tension/load forces that a tendon may place upon the repair device 20 is depicted. In addition, the graph depicts the strainability of prior art devices, such as suture techniques or other prior art devices, represented along reference line 102. Further, the graph depicts the strainability of a native tendon or original tendon that hasn't been damaged, shown along reference line 104. Now with reference to FIGS. 1 and 6, the graph also represents various sections along length X that correspond with various portions along the length 26 of the repair device 20. For example, the graph depicts a first section 106, a second section 108, and a third section 110, which correspond to the first portion 30, the second portion 32, and the intermediate portion 34 of the repair device 20, respectively. The first section 106, corresponding to the first portion 30 of the repair device 20, depicts the strain € increasing (to the left) along the length 26 of the first portion 30 from the intermediate portion 34 to the first end 46 of the first portion 30. Likewise, the second section 108, corresponding to the second portion 32 of the repair device 20, depicts the strain € increasing (to the right) along the length 26 of the second portion 32 from the intermediate portion 34 to the second end 48 of the second portion 32. The third section 110, which corresponds to the intermediate portion 34 of the repair device 30, depicts minimized strainability and a substantially constant strain €. As depicted, the first and second portions 30, 32 of the repair device 20 include structure to facilitate strainability or elongation along the length 26 of the repair device 20. Such elongation of the first and second portions 30, 32 attached to a tendon 10 facilitates the tendon to elongate to allow the tendon to function similarly to that of the native tendon while the intermediate portion 34 of the repair device 20 substantially removes the load from the repair site of the lacerated tendon and prevents elongation to facilitate the healing process.

Figure 7:
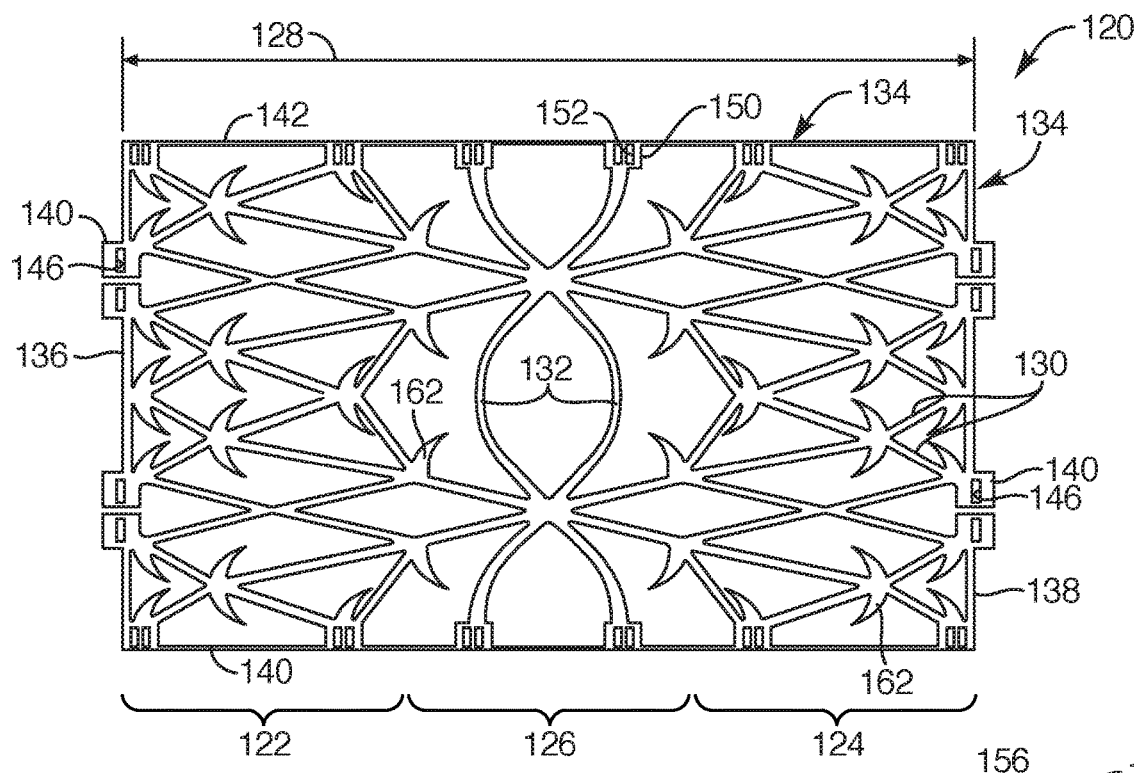
FIG. 7 is a top view of a repair device prior to being formed into a tubular configuration, according to another embodiment of the present invention.
Figures 7A, 8:
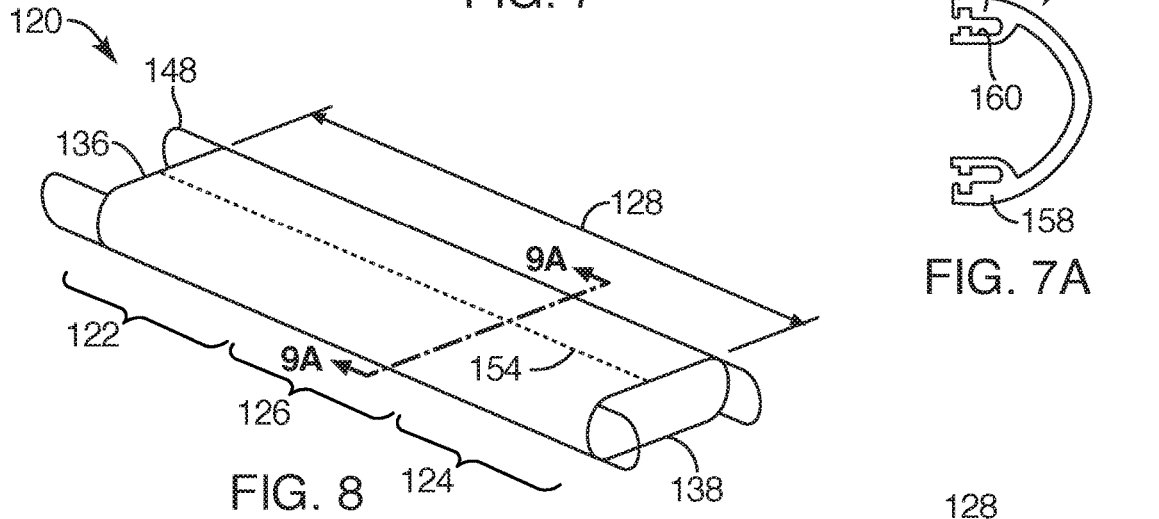
FIG. 7A is a side view of an end crimp, according to another embodiment of the present invention.
FIG. 8 is a simplistic perspective view of the repair device of FIG. 7, depicting the repair device formed into a tubular configuration with end crimps at the ends of the repair device, according to another embodiment of the present invention.

Now referring to FIGS. 7 and 8, another embodiment of a soft tissue repair device 120 is provided. Similar to the previous embodiment, the repair device 120 includes a first portion 122 and a second portion 124 with an intermediate portion 126 therebetween, each portion extending along a longitudinal length 128 of the repair device 120. The first and second portions 122, 124 include structure to facilitate elongation and strainability along the length of the respective first and second portions 122, 124. Also, the intermediate portion 126 may resist strain or elongation its length of the repair device 120. As such, the first and second portions 122, 124 and intermediate portion 126 respond similar to respective first and second sections 106 and 108 and third section in the graph of FIG. 6. Further, as in the previous embodiment, the repair device 120 may include interconnecting struts 130 defining a multi-cellular structure. The struts 130 extending over the length of the first and second portions 122, 124 may be sized and configured to facilitate elongation along the length thereof. Further, the struts 130 extending over the length of the intermediate portion 126 may be sized and configured to substantially resist elongation. The intermediate portion 126 may include laterally extending struts 132. Such laterally extending struts 132 may serve to cage the tendon (not shown) or substantially prevent the end portions of the severed tendon from trumpeting beyond the struts at the intermediate portion 126 of the repair device 120.

In this embodiment, the repair device 120 may primarily be a one piece member and may be cut from a flat sheet of, for example, super-elastic material, such as Nitinol or the like, and then formed into a tubular configuration. In the pre-formed configuration, the repair device 120 may include a peripheral edge 134 with a first end edge 136, a second end edge 138, a first side edge 140 and a second side edge 142. The first and second end edges 136, 138 may include end coupling portions in the form of tabs 144. The tabs 144 may define tab openings 146 sized and configured to couple to end crimps 148. The first and second side edges 140, 142 may also include side coupling portions. Such side coupling portions may include side tabs 150 defining side openings 152. Once the repair device 120 is formed in the tubular configuration, the first side edge 140 may be positioned to abut the second side edge 142 and coupled together via the side openings 152 of the respective first and second side edges 140, 142 to provide a seam 154, shown in outline form in FIG. 8. Such coupling may be employed with crimps, ties, zip-ties, or any other suitable coupling mechanism as known in the art.

Now with reference to FIGS. 7, 7A and 8, one embodiment of an end crimp 148 is provided. The end crimp 148 may include a c-shaped configuration. The end crimp 148 may include an upper end 156 and a lower end 158, each end defining a notch configuration 160 sized and configured to couple to the tab openings 146 defined in the tabs 144 at the first end edge 136 and the second end edge 138 once the repair device 120 has been formed into the tubular configuration. Further, the end crimps 148 may be sized and configured to act as a clamp. As such, once a tendon is positioned within the repair device 120, the end crimps 148 may be sandwiched or, in other words, the upper end 156 and the lower end 158 may be moved closer together to clamp down over the tendon. Such crimping or clamping may minimize potential migration from the repair device when the tendon elongates under a load/tensional force. The end crimps 148 may be a laser cut from a flat sheet of metallic material, such as stainless steel or the like, or any other bio-compatible material as known in the art that will substantially maintain a crimped or clamped position.

As previously set forth, the repair device 120 may be formed into a tubular configuration from a flat sheet of, for example, super-elastic material, such as Nitinol. Such may be employed by positioning the flat repair device 120 within or around a jig and heat-setting the repair device 120 in the tubular configuration with the tines 162 oriented substantially orthogonally inward or at an acute angle to extend inward and toward the intermediate portion 126, as known in the art. The tubular configuration may include a cross-section with any appropriate configuration, depending on the particular soft tissue to be repaired. For example, most tendons include an oval cross-section and, as such, the cross-section of the tubular configuration may include a rectangular or oval configuration. However, some tendons include a circular cross-section and, as such, a square or circular configuration may be appropriate. As previously set forth, once heat-set and formed into the desired configuration, the opposing first and second edges may then be coupled together to form the seam 154 and the end crimps 148 may then be assembled to the repair device 120.

Figure 9A:
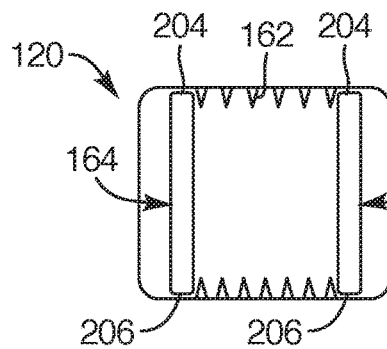
FIG. 9A is a cross-sectional view of the repair device taken from section 9A of FIG. 9, according to an embodiment of the present invention.
Figure 9B:
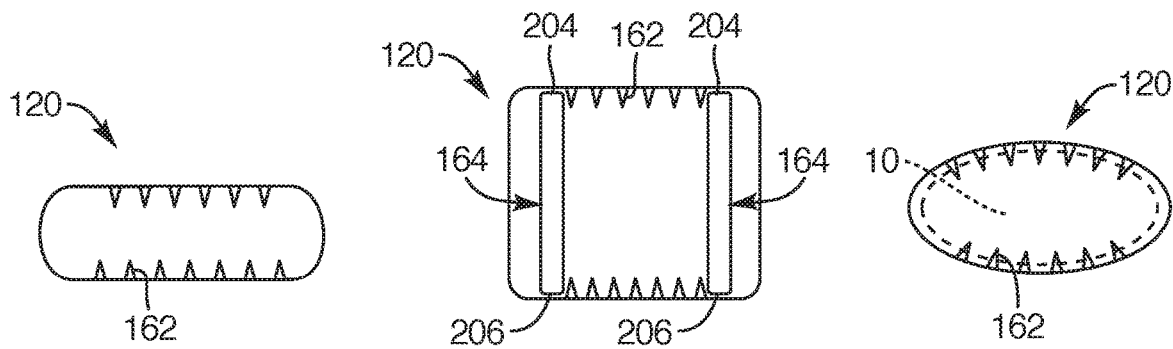
FIG. 9B is the sectional view of the repair device shown in FIG. 9A, depicting an applicator expanding the repair device, according to another embodiment of the present invention.
Figure 9C:
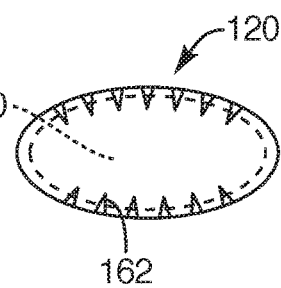
FIG. 9C is the sectional view of the repair device shown in FIG. 9A, depicting the applicator removed and conforming to a tendon positioned within the repair device, according to another embodiment of the present invention.

With respect to FIGS. 9A, 9B, and 9C, the method steps for employing the repair device 120 with a tendon 10 are provided. For example, FIG. 9A depicts a sectional view of FIG. 9, depicting the repair device 120 in a first position and in its heat-set relaxed state. With respect to FIG. 9B, prior to inserting, for example, a lacerated tendon 10 into the repair device 120, the repair device can be expanded. Such expansion may be employed by inserting an applicator 164 at each end of the repair device 120 to move the repair device 120 to a second position or into an expanded, stressed position. Once expanded, the tubular configuration is broadened or provides a larger cross-sectional opening along the length (not shown) of the repair device 120. Such expanded position efficiently facilitates pulling a first tendon end and a second tendon end with, for example, a suture (not shown), into the repair device 120 while minimizing potentially damaging the tendon on the tines 162. Once the tendon 10 is appropriately positioned within the expanded repair device 120, the applicators 164 may be removed from each end of the repair device 120. The repair device 120 will then automatically move toward its relaxed state or third position and conform around the tendon 10 with the tines 162 engaging the tendon 10, as depicted in FIG. 9C. The end crimps 148, shown in FIG. 8, may then be crimped or clamped to minimize potential migration of the tendon 10 from the repair device 120.

Figure 10:
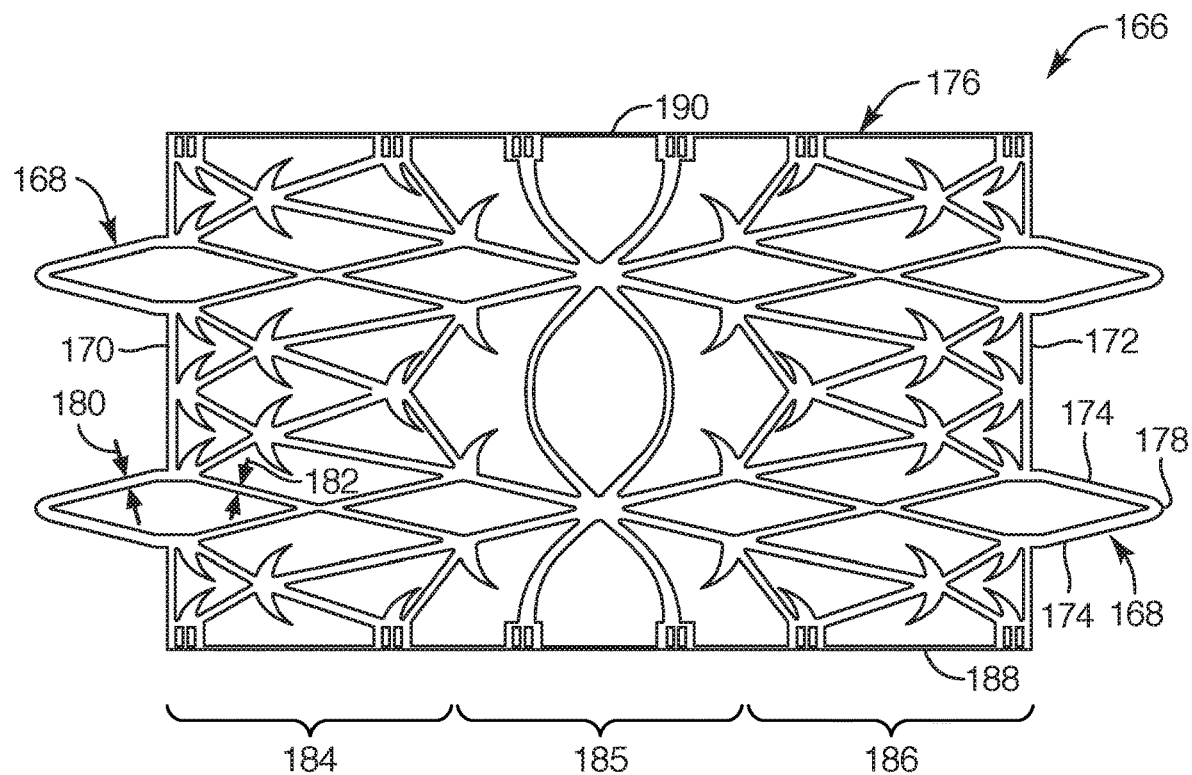
FIG. 10 is a top view of a repair device prior to being formed into a tubular configuration, according to another embodiment of the present invention.
Figure 11:
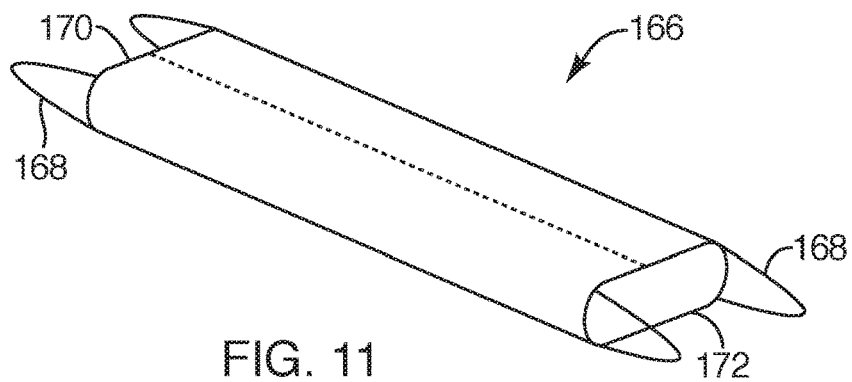
FIG. 11 is a simplistic perspective view of the repair device of FIG. 10, depicting the repair device formed into a tubular configuration with end springs at the ends of the repair device, according to another embodiment of the present invention.

Now with reference to FIGS. 10 and 11, another embodiment of a repair device 166 is provided. This embodiment is similar to the previous embodiment of FIGS. 7 and 8 in most all respects, except instead of end crimps, this embodiment includes spring portions 168. The spring portions 168 may be sized and configured to resist the ends of the repair device 166 widening under stresses the repair device 166 may undergo while also allowing an applicator (not shown) to expand the tubular configuration in preparation for inserting and positioning a tendon within the repair device 166. The spring portions 168 may extend generally from a periphery 176 of the repair device and, more specifically, from a first end edge 170 and a second edge 172 with a v-shaped configuration. Other configurations may also be employed to control stresses within the tubular configuration of the repair device 166. The spring portion 168 may include spring extensions 174 extending from the periphery 176 of the repair device 166 and extend to a common portion 178 to form the v-shaped configuration. The spring extensions 174 may include an extension width 180 that is greater than a width 182 of the struts 183 of the first portion 184 and the second portion 186 of the repair device 166. Struts 183 in the intermediate portion 185 may be similarly sized or may be greater than the width 182 of the struts 183 of the first and second portions 184, 186. With this arrangement, the repair device 166 may be formed from a single piece of, for example, super-elastic material, except for any potential side crimps for coupling the first and second side edges 188, 190 to form the repair device 166 in the tubular configuration. Further, as in the previous embodiments, an important aspect of the present invention is that the first and second portions 184, 186 may elongate along the length of the repair device 166 and respond with a stainability characteristic similar to that shown in respective first and second sections of the graph of FIG. 6. Likewise, the intermediate portion 185 structurally minimizes strainablity and elongation along the length of the repair device 166 to respond similar to the third section of the graph of FIG. 6.

Figure 12:
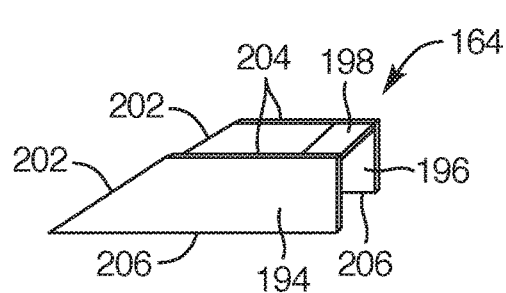
FIG. 12 is a perspective view of an adapter, according to an embodiment of the present invention.

FIG. 12 depicts one embodiment of the before mentioned applicator 164 that may be employed with either of the embodiments shown in FIGS. 8 and 11. With respect to FIGS. 8, 11, and 12, the applicator 164 may include a first side rail 194 and a second side rail 196 with a bridge portion 198 therebetween for joining the first and second side rails 194, 196. Each of the first and second side rails 194, 196 may include a tapered portion 202 to assist in the insertion of the applicator 164 in the tubular configuration of the repair device 120, 166. The first and second side rails 194, 196 each also include an upper edge 204 and lower edge 206. Upon inserting the applicator 164 into the tubular configuration, the tapered portion 202 assists in expanding the tubular configuration to expand the repair device 120 over the upper edge 204 and lower edge 206 of the applicator 164, as depicted in FIG. 9B.

Figure 13:
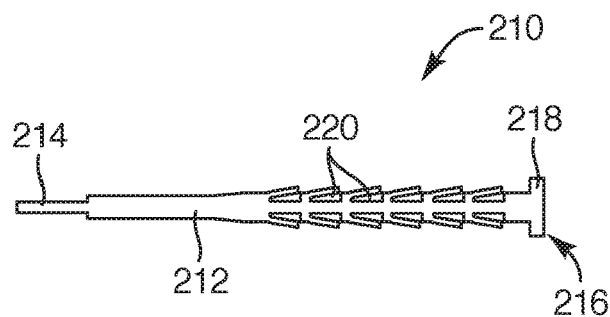
FIG. 13 is a side view of a zip tie, according to another embodiment of the present invention.

FIG. 13 depicts an enlarged view of a zip tie 210. The zip tie 210 is another embodiment that may be employed for coupling ends together at the before mentioned tabs of the repair device. The zip tie 210 may replace the various crimps discussed herein. The zip tie may include an elongated body 212 with a leading end 214 and a trailing end 216 with a back stop 218. The elongated body 212 may include tapered extensions 220 extending therefrom such that the tapered extensions 220 taper towards the leading end 214. The zip tie 210 may be sized and configured such that the leading end 214 can be pulled through the side openings 152 defined in the side tabs 150 of, for example, the tabs 150 of the first and second side edges 140, 142 of the repair device 120 depicted in FIG. 7. Once pulled through the side openings 152 and tightened to a desired position, the excess portion of the zip tie 210 may then be trimmed.

In another embodiment, in addition to, or instead of, the before-mentioned crimps or zip tie, sutures or a wire (not shown), such as a Nitinol wire may be employed to maintain the repair device in the engaging position or second position. For example, in the embodiment shown in FIGS. 1 through 4, rather than employing the side crimps 70, the upper frame portion 38 and the lower frame portion 40 may be coupled together with a suture or flexible wire in a shoe-lace arrangement such that once the upper and lower frame portions 38, 40 are positioned over the tendon 10 the suture or flexible wire may be synched to move the upper and lower frame portions 38, 40 to the second engaging position, as depicted in FIG. 4. The suture and/or wire may be pre-weaved through the appropriate tabs to move the respective frame portions to the second position or be laced through the tabs during the surgical procedure. Such suture and/or wire may be employed in any of the other embodiments described herein, for example, the suture and/or wire may be employed to replace the end crimps 148 depicted in FIGS. 7A and 8.

With reference to FIGS. 14 and 14A, another embodiment of a repair device 310 is depicted. In this embodiment, the repair device 310 includes a first portion 312, a second portion 314 and an intermediate portion 316 therebetween that define a bore 318 and an axis 320 extending through the repair device 310 and along a longitudinal length 324 of the repair device 310. The first and second portions 312, 314 may be referenced as moveable or elongateable portions and the intermediate portion 316 may be referenced as a stabilizing portion sized and configured to resist elongation. In other words, the first and second portions 312, 314 may be configured to move and elongate as a load is placed on the tendon while the intermediate portion 316 may be configured to stabilize tendon ends to be abutted and maintained against each other in a substantially fixed position such that the intermediate portion is also in a substantially fixed position relative to the tendon ends and resists elongation along a length of the intermediate portion. Further, in this embodiment, the first portion 312 and the second portion 314 are two separate tubular frame structures connected with one or more wires 322 interlaced through apertures (not shown) defined at ends the first portion 312 and second portion 314 of the repair device 310, the one or more wires 322 defined as the intermediate portion 316. As will be discussed in further detail below, the longitudinal length 324 of the repair device 310 may be minimized upon application of the repair device 310 to a first tendon portion and a second tendon portion (not shown) such that the intermediate portion 316 will be tightened over lacerated ends of the tendon and minimized along its length.

The first and second portions 312, 314 of the repair device 310 may be laser cut from, for example, a metallic material, such as stainless steel or a super-elastic material. For example, in one embodiment, the repair device may be cut from a flat sheet or tube of super-elastic material, such as Nitinol or the like. In the example of the super elastic material, once laser cut, the components of the repair device may undergo various processes, such as electro-polishing and, if necessary, heat-set in, for example, a heated sand bath to a desired position, as known to one of ordinary skill in the art. Further, the wire may be a metallic material, such as Nitinol or stainless steel.

The first portion 312 may include multiple interconnecting struts 326 to define a multi-cellular structure. The interconnecting struts 326 may extend from the intermediate portion 316 to a first end 328 of the repair device 310 and extend in a tubular configuration to define a portion of the bore 318 extending therethrough. Likewise, the second portion 314 may include the multiple interconnecting struts 326 to define a multi-cellular frame structure and extend from the intermediate portion 316 to a second end 330 of the repair device 310, extending with a tubular configuration to define a portion of the bore 318 of the repair device 310.

Each of the first portion 312 and the second portion 314 may include tines 332 or hooks extending from nodes 334 or junction points of the interconnecting struts 326. The nodes 334 or a node may be defined as the junction of one strut 326 interconnecting to one or more adjacent struts 326, the tines 332 extending from such nodes 334, similar to that set forth in previous embodiments. The tines 332 may extend inward toward the axis 320 of the repair device 310. In another embodiment, the tines 332, of both the first portion 312 and the second portion 314, may extend inward toward the axis 320 and toward the intermediate portion 316 such that the tines 332 of the first portion 312 are oriented in a first direction and the tines of the second portion 314 are oriented in a second direction, similar to that set forth in previous embodiments. In one embodiment, each node 334 may include one or more tines 332 extending therefrom. In another embodiment, the tines 332 may extend from nodes 334 along an upper portion 336 and a lower portion 338 of the repair device 310.

Now with reference to FIGS. 15 through 18, the steps for applying and securing the repair device 310 to a lacerated tendon will now be described. With respect to FIG. 15, the repair device 310 may be removed from sterile packaging (not shown) along with, for example, two needle point suture loops 340, 342 (see FIG. 16). The repair device 310 may be pre-loaded with the first portion 312 over a first applicator 344 and the second portion 314 over a second applicator 346 (see also the description of FIG. 12 of one example of an applicator). Otherwise, the physician may load the first and second portions 312, 314 of the repair device 310 to the first and second applicators 344, 346, respectively. With the repair device 310 positioned over the first and second applicators 344, 346, the repair device 310 is expanded to an orientation or shape that radially enlarges the bore 318 of the repair device 310 to readily facilitate inserting the lacerated tendon into the repair device 310.

Figure 16:
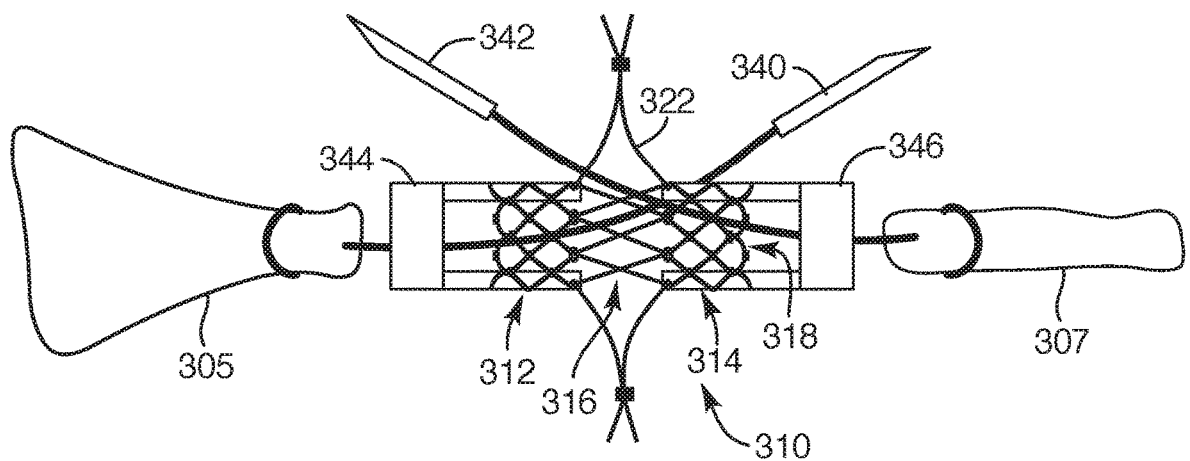
FIG. 16 is a top view of the repair device, depicting the repair device being applied to a lacerated tendon by pulling the tendon ends into the repair device via suture needle loops, according to another embodiment of the present invention.
Figure 17:
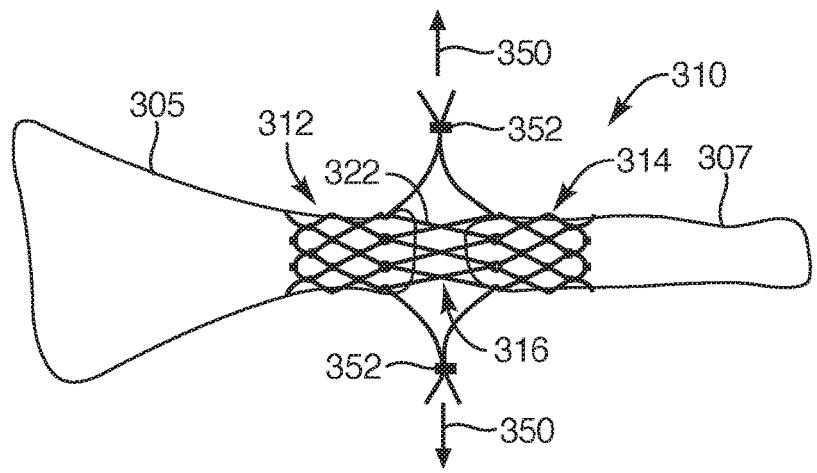
FIG. 17 is a top view of the repair device, depicting the repair device positioned over a lacerated tendon upon the applicators and suture needle loops are removed, according to another embodiment of the present invention.

As depicted in FIGS. 16 and 17, the first and second needle point suture loops 340, 342 may be passed through and secured to the first tendon portion 305 and a second tendon portion 307, respectively, employing suturing techniques as known to one of ordinary skill in the art. The repair device 310 may then be positioned between the first and second tendon portions 305, 307. The first tendon portion 305 may then be pulled through the bore 318 of the first portion 312 of the repair device 310 by pulling the secured first suture loop 340 into the bore so that the end of the first suture loop 340 is passed through the wires 322 of the intermediate portion 316, as depicted. Similarly, the second tendon portion 307 may then be pulled into the bore 318 of the second portion 314 of the repair device 310 via the second suture loop 342. Once the first tendon portion 305 is positioned within the bore 318 of the first portion 312 of the repair device 310, the first applicator 344 can be removed and the first suture loop 340 may be removed or cut from the first tendon portion 305. Likewise, upon the second tendon portion 307 being positioned within the bore 318 of the second portion 314 of the repair device 310, the second applicator 346 and second suture loop 342 may be removed, as depicted in FIG. 17. Upon the first and second applicators 344, 346 being removed from the first and second tendon portions 305, 307, the radial dimension or height of the bore 318 automatically is minimized along a length of the first and second portions 312, 314 of the repair device 310 such that the tines 332 (FIG. 14A) engage the tendon to anchor the repair device thereto.

Figure 18:
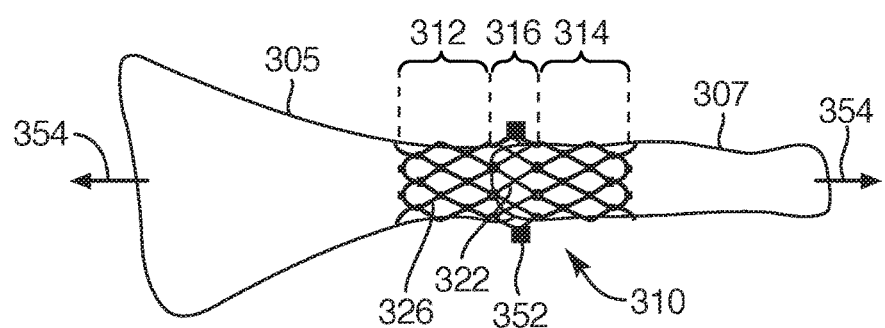
FIG. 18 is a top view of the repair device, depicting an intermediate portion of the repair device synched to abut ends of the lacerated tendon, according to another embodiment of the present invention.

At this juncture, with reference to FIGS. 17 and 18, the one or more wires 322 of the intermediate portion 316 may be pulled by the physician, as indicated by arrows 350, so as to pull the first portion 312 and the second portion 314 closer to each other. Further, such pulling of the one or more wires 322 pulls respective ends of the first and second tendon portions 305, 307 against each other in an abutted arrangement. The one or more wires 322 may include one or more swages 352 or crimps that can be tightened down over the one or more wires 322 to maintain the first and second tendon portions 305, 307 against each other. With this arrangement, the intermediate portion 316 of the repair device 310 substantially maintains the ends of the respective first and second tendon portions 305, 307 in the abutted arrangement while the first portion 312 and the second portion 314 is anchored or harnessed to the lacerated tendon via the tines 332.

With respect to FIGS. 6 and 18, similar to previous embodiments, the multi-cellular frame structure of the first portion 312 and second portion 314 of the repair device 310 may elongate upon a load being placed upon the tendon while the intermediate portion 316 substantially prevents elongation of the ends of the first and second tendon portions 305, 307, maintaining such ends to in the abutted arrangement. For example, similar to previous embodiments, the structural characteristics of the interconnecting struts 326 extending along the first portion 312 and the second portion 314 of the repair device 310 may be sized and configured (e.g., by tapering along their lengths or varying the thickness of the struts or varying the angle of the struts, arcuate portions along lengths of struts (cell configuration), material properties, etc.) to facilitate elongation upon a load being placed upon the tendon. In this manner, the first portion 312 and the second portion 314 may strain or elongate along their respective lengths similar to that depicted in sections 106 and 108, respectively, of the strain-length graph of FIG. 6. Similarly, the intermediate portion 316, made of one or more wires 322 interlaced with the first and second portions 312, 314 of the repair device 310, may be sized and configured to substantially prevent or resist strain or elongation along the intermediate portion 316 of the repair device 310, similar to that depicted in section 110 of the strain vs. length graph of FIG. 6. With this arrangement, the repair device 310 can facilitate elongation of a loaded tendon while also maintaining the lacerated ends of the first and second tendon portions 305, 307 in the abutted arrangement.

Now with reference to FIGS. 19-22, another embodiment of a repair device 410 configured to harness and repair a lacerated tendon 403 is depicted. This embodiment is similar to the previous embodiment in that the repair device 410 includes separate portions coupled together, such as a first part 426 and a second part 427 with one or more wires 418 coupling the first part 426 to the second part 427, except this embodiment may not include integrally formed anchors/tines, but rather, the repair device 410 of this embodiment may employ separate and discrete anchoring components, such as staples 472 (FIG. 22), to anchor the repair device 410 to the tendon 403.

Figure 19:
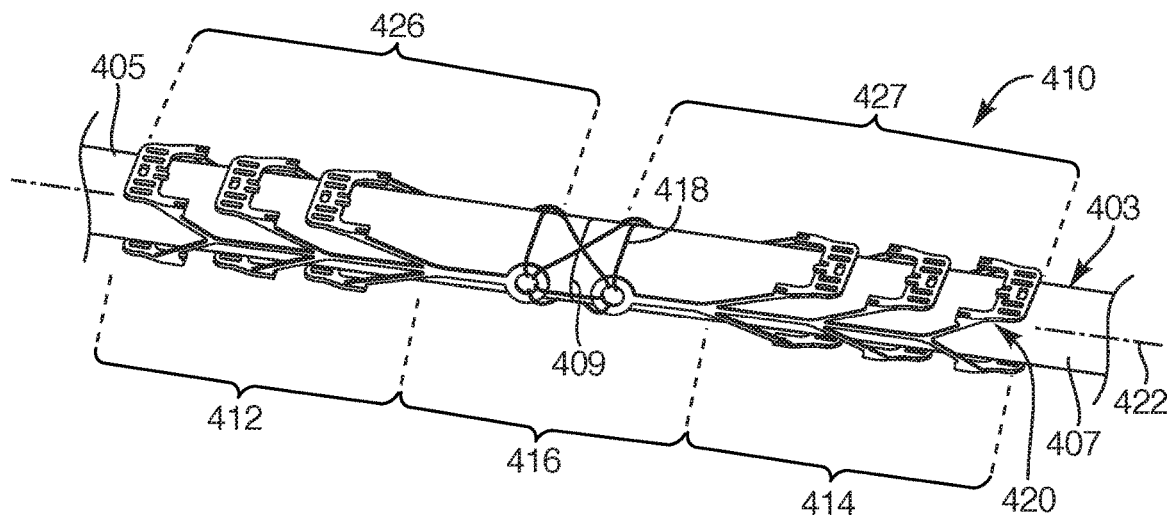
FIG. 19 is a perspective view of another embodiment of a repair device, depicting the repair device coupled to a lacerated tendon, according to the present invention.

With respect to FIG. 19, the repair device 410 may include a first portion 412, a second portion 414 and an intermediate portion 416 extending between the first and second portions 412, 414, the intermediate portion 416 including, among other portions, the one or more wires 418. As in the previous embodiments, the first and second portions 412, 414 may be referenced as moveable or elongateable portions and the intermediate portion 416 may be referenced as a stabilizing portion that is sized and configured to resist elongation. In other words, the first and second portions 412, 414 may be configured to move and elongate (or even move to an arcuate position) as a load is placed on the tendon while the intermediate portion 416 may be configured to stabilize tendon ends to be abutted and maintained against each other in a substantially fixed position with the intermediate portion 416 also in a substantially fixed position relative to the tendon ends such that the intermediate portion 416 resists elongation along a length of the intermediate portion.

Further, the first part 426 may define the first portion 412 and a portion of the intermediate portion 416. Similarly, the second part 427 may define the second portion 414 and another portion of the intermediate portion 416. The first portion 412 and the second portion 414 may be sized and configured to be positioned over a first tendon portion 405 and a second tendon portion 407, respectively, and the intermediate portion 416 of the repair device 410 may be configured to span and be positioned over abutted ends 409 and end portions of the lacerated tendon 403. As in previous embodiment, the repair device 410 may define a bore 420 and an axis 422 each extending longitudinally through the repair device 410 to receive the lacerated tendon 403. With this arrangement, the repair device 410 may act as a harness type structure for a lacerated tendon 403 with first and second portions 412, 414 that dynamically move relative to the variable loads and movement made by the tendon and with the intermediate portion 416 controlling and minimizing movement of the abutted ends 409 of the lacerated tendon 403.

The structure of the repair device 410 may include various struts, extensions, and/or portions, some of which may define a multi-cellular structure, each having a particular function described in detail herein. Further, the first part 426 and the second part 427 of the repair device 410 may be laser cut from, for example, a tube of super-elastic material, such as Nitinol. As such, the first and second parts 426, 427 of the repair device 410 may each be its own unitary and monolithic structure having been made from a single piece of tube. Once laser cut, the first and second parts 426, 427 of the repair device 410 may undergo various processes, such as electro-polishing and, if necessary, heat-set in, for example, a sand bath to a desired position, as known to one of ordinary skill in the art. The one or more wires 418 may be metallic, such as Nitinol or stainless steel, or any other suitable and biocompatible material. In another embodiment, the first and second parts 426, 427 of the repair device may not be separated as two components, but rather, formed from a single tube of material and formed as a unitary, seamless, monolithic structure With respect to FIGS. 20 and 21, for simplification purposes, only the first part 426 defining the first portion 412 and a first intermediate portion 424 of the repair device 410 is depicted, although the second part 427 (FIG. 19) may be a mirror image of the first part 426 and may be substantially similar in functionality, parts, and portions in all respects. The first part 426 of the repair device 410 may include a first side 428, a second side 430, an upper side 432 and a lower side 434 defining the axis 422 and the bore 420 extending axially therethrough and extending between a first end 436 and a second end 438 of the first part 426. The first side 428 and the second side 430 may each include a tree-like structure having a trunk 440 and multiple branches 442. Each trunk 440 of the first part 426 of the repair device 410 may define the first intermediate portion 424. Further, each trunk 440 may include a width 444 that is larger than a branch width 446. Each trunk 440 may extend between the second end 430 and the branches 442 or, otherwise referred to, the first portion 412 of the repair device 410, the second end 438 of the first part 426 defining an eyelet 448 for lacing the before-mentioned one or more wires 418 (FIG. 19).

Further, the trunk 440 may be proportionately smaller or larger in length relative to the first portion 412 than that which is depicted.

As previously set forth, each of the first and second sides 428, 430 may include the trunk 440 with multiple branches 442, each extending with a substantially similar profile and pattern. For example, the branches 442 may include a first branch set 450, a second branch set 452 and a third branch set 454, each extending from a junction point 456. The first branch set 450 may extend directly from the trunk 440 or the junction point 456 between the trunk 440 and the first branch set 450. The first branch set 450 may include an upper branch 442a, a middle branch 442b and a lower branchb442c. The upper branch 442a may extend at an angle relative to the middle branch 442b, extending upward and toward the first end 436 of the first part 426 of the repair device 410. The lower branch 442c may extend at a similar angle, but a mirror image of the upper branch 442a, extending downward and toward the first end 436 of the first part 426 of the repair device 410. The middle branch 442b may extend toward the first end 436 and parallel with the axis 422 of the repair device 410. Further, the middle branch 442b of the first branch set 450 may extend toward the junction point 456 of the second branch set 452. The first branch set 450 and the second branch set 452 may extend similar to each other, the second branch set 452 including the middle branch 442b that extends to the third branch set 454. In one embodiment, the third branch set 454 may include the upper branch 442a and the lower branch 442c, without the middle branch 442b. In another embodiment, the third branch set 454 may include the middle branch 442b that extends to a fourth branch set (not shown). This may be repeated with additional branch sets depending on the desired extending branch sets for a given length of the first part 426 of the repair device 410.

As previously set forth, each of the first side 428 and second side 430 of the first part 426 of the repair device 410 may extend similarly to each other with respective trunks 440 and branches 442. With that stated, the first side 428 and the second side 430 may be coupled to each other with lateral extensions 458 or pad portions extending between respective upper branches 442a and lower branches 442c of each of the branch sets. For example, the upper branch 442 of the first branch set 450 on each of the first side 428 and the second side 430 of the first part 426 of the repair device 410 may extend to one lateral extension 458 or, more specifically, an upper pad portion 460. Likewise, the lower branch 442c of the first branch set 450 on each of the first side 428 and second side 430 of the repair device 410 may extend to another lateral extension 458 or a lower pad portion 462. Each branch set may similarly extend with its upper branch 442a and lower branch 442c to an upper pad portion 460 and a lower pad portion 462, respectively. The upper and lower pad portions 460, 462 may at least partially define the upper side 432 and the lower side 434 of the first part 426 of the repair device 410. Each pad portion may include an inner surface 464 and an outer surface 466, the inner surface 464 facing the axis 422 of the repair device 410. Further, the upper pad portion 460 may directly face the lower pad portion 462. For example, the upper branch 442a of the first branch set 450 extends to the upper pad portion 460 and the lower branch 442c of the first branch se 450t extends to the lower pad portion 462 such that the inner surfaces 464 of the upper pad portion 460 and the lower pad portion 462 correspond and face each other. The upper and lower pad portions 460, 462 of the second and third branch sets 452, 454 may be similarly arranged. In addition, the outer surfaces 466 of the upper and lower pad portions 460, 462 may face directly away from each other. The inner and outer surfaces 464, 466 of each of the pad portions may be substantially planar. In one embodiment, the inner and/or outer surfaces 464, 466 may include one or more atraumatic tabs that may protrude from the surfaces for aligning purposes.

Each of the upper and lower pad portions 460, 462 may include one or more through holes 468 and one or more indents 470 in the form of a notch extending through a portion of the pad. For example, each pad portion may define two pair of holes 468 extending through the pad portion such that the holes 468 of the upper pad portion 460 correspond and are aligned with the holes 468 of the corresponding lower pad portion 462. Further, the outer surface 466 (or the inner surface) of each of the pad portions may include the indents 470 or atraumatic tabs sized and configured to align each upper pad portion 460 with its corresponding lower pad portion 462 when expanded with, for example, an applicator (not shown). In the case of employing indents 470 for aligning purposes, the applicator may include tabs that may fit and align within the indents 470 to properly align the device within the applicator. In the case of tabs, the applicator may have corresponding tabs or indents to facilitate proper alignment of the repair device within the applicator. Further description of the holes 468 and indents 470 or notches will be provided hereafter.

Figure 20:
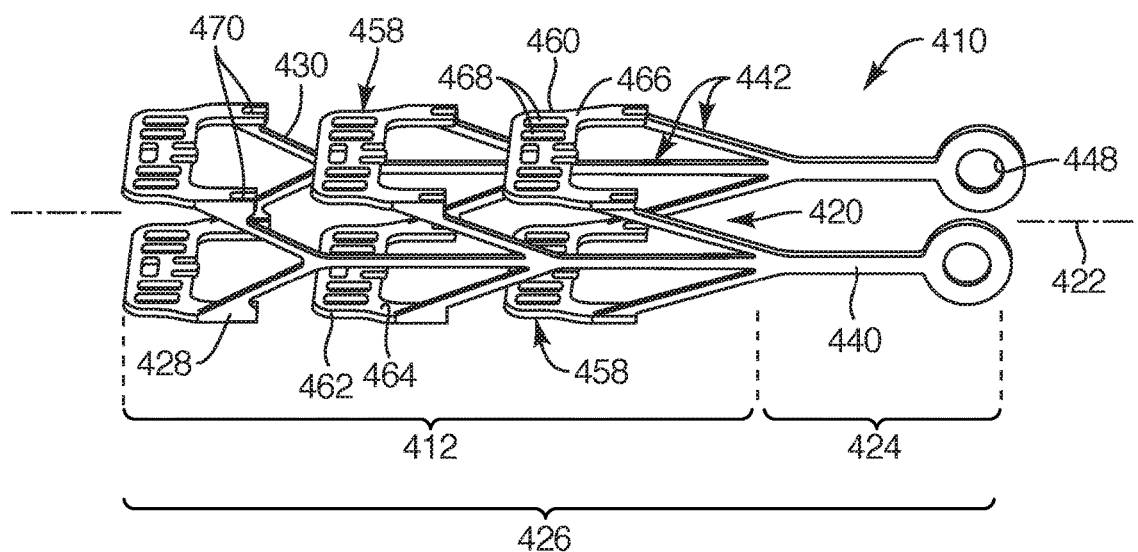
FIG. 20 is a perspective view of a first part of the repair device of FIG. 19, depicting the repair device in a non-strained position, according to another embodiment of the present invention.
Figure 21:
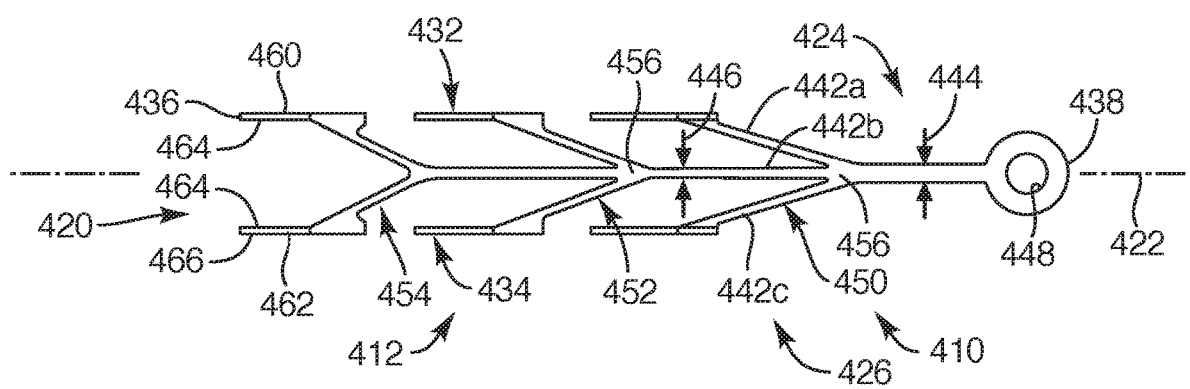
FIG. 21 is a side view of the first part of the repair device, depicting a side profile of the first part of the repair device, according to another embodiment of the present invention.
Figure 22:
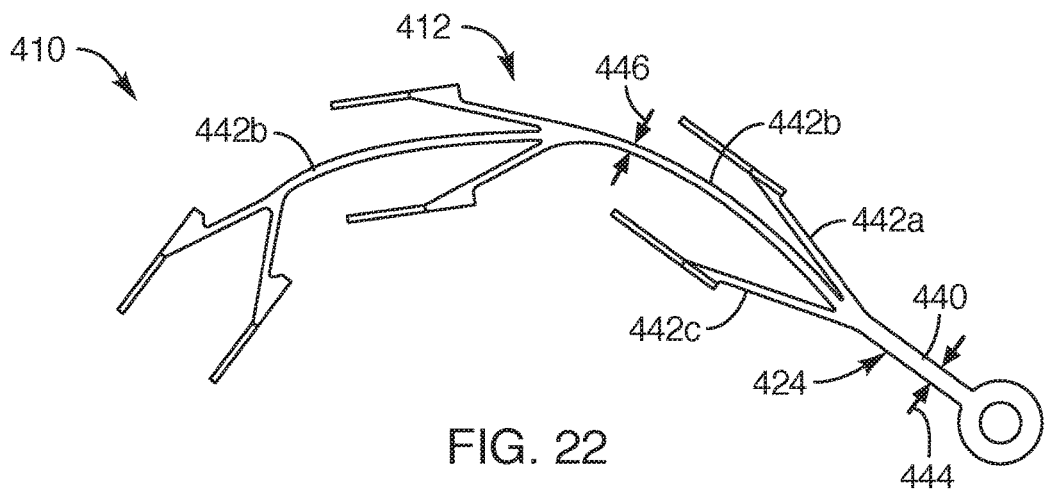
FIG. 22 is a side view of the first part of the repair device, depicting the first part of the repair device moved to an arcuate position, according to another embodiment of the present invention.

With respect to FIGS. 20 and 22, as previously set forth, the first intermediate portion 424 or trunk 440 includes a width 444 greater than the branch width 446 of each middle branch 442b and may also be greater than a width of each upper and lower branches 442a, 442c. The width 444 of the trunk 440 may be sized and configured to stabilize the ends of the lacerated tendon 403 (see FIG. 19). Further, such width 444 may be sized to minimize bending of the trunk so that movement of a portion of the tendon 403 situated along the first intermediate portion 424 is also minimized. With that being said, the middle branches 442b extending along the first portion 412 of the repair device 410 may be sized and configured to facilitate bending or to facilitate the first portion 412 of the repair device 410 to be moveable to an arcuate position or moveable with a tight radial turn, such as up to a 90 degree angle. Such bending may be useful depending on the type of tendon 403 being repaired, such as a digit tendon along one's finger. Further, the upper and lower branches 442a, 442c of each branch set may be sized and configured to bend and correspond with the arcuate position of the middle branch 442b. Further, the upper and lower branches 442a, 442c of each branch set may be sized and configured to facilitate elongation of the first portion 412 as a load is placed upon the tendon 403 to which the first portion 412 is attached and the tendon naturally wants to elongate and/or move along a bend. As in previous embodiments, as the first portion 412 elongates and facilitates elongation of the tendon 403, the intermediate portion 416 or first intermediate portion 424 substantially prevents elongation to minimize movement at the ends of the lacerated tendon 403. Further, as in previous embodiments, the first portion 412 may elongate with a strain gradient similar to that shown in the corresponding section 106 of FIG. 6. Similarly, the intermediate portion 416 of the repair device 410 may be sized and configured to substantially prevent or resist strain and elongation along that portion of the repair device 410 similar to that shown in section 110 of FIG. 6 and, therefore, substantially prevents separation of the ends of the lacerated tendon 403. As set forth previously, the first part 426 of repair device 410 is a mirror image of a second part 427 of the repair device 410, as depicted in FIG. 19 and, therefore, may structurally behave in a similar manner.

Figure 23:
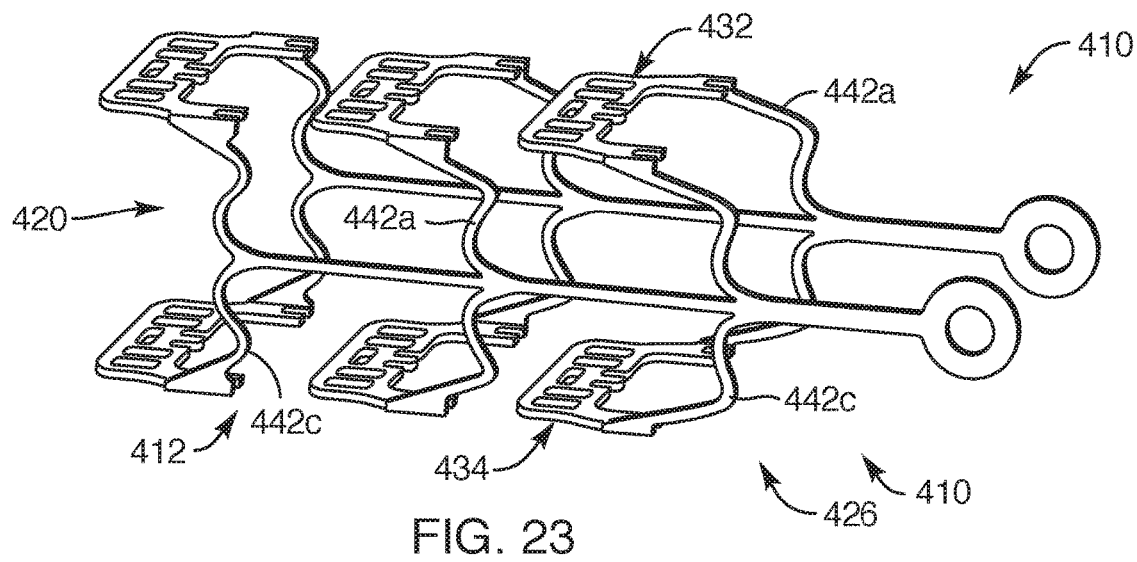
FIG. 23 is a perspective view of the first part of the repair device, depicting the repair device in a strained position as if loaded in an applicator, according to another embodiment of the present invention.

With respect to FIG. 23, the first part 426 of the repair device 410 is depicted in a strained position. It is noted that the second part (not shown) of the repair device 410 may be similarly moved to the strained position. The first part 426 of the repair device 410 may be moved to the strained position with an applicator (not shown) similar to that provided in previous embodiments. In the strained position, the upper and lower branches 442*a*, 442*c* of each branch set may be moved to extend upward and downward, respectively, toward the respective upper side 432 and lower side 434 of the repair device 410. In this manner, the bore 420 extending through the first portion 412 of the repair device 410 may be enlarged to readily facilitate pulling a first tendon portion (not shown) through the bore 420, similar to that depicted in the previous embodiment.

Figure 24:
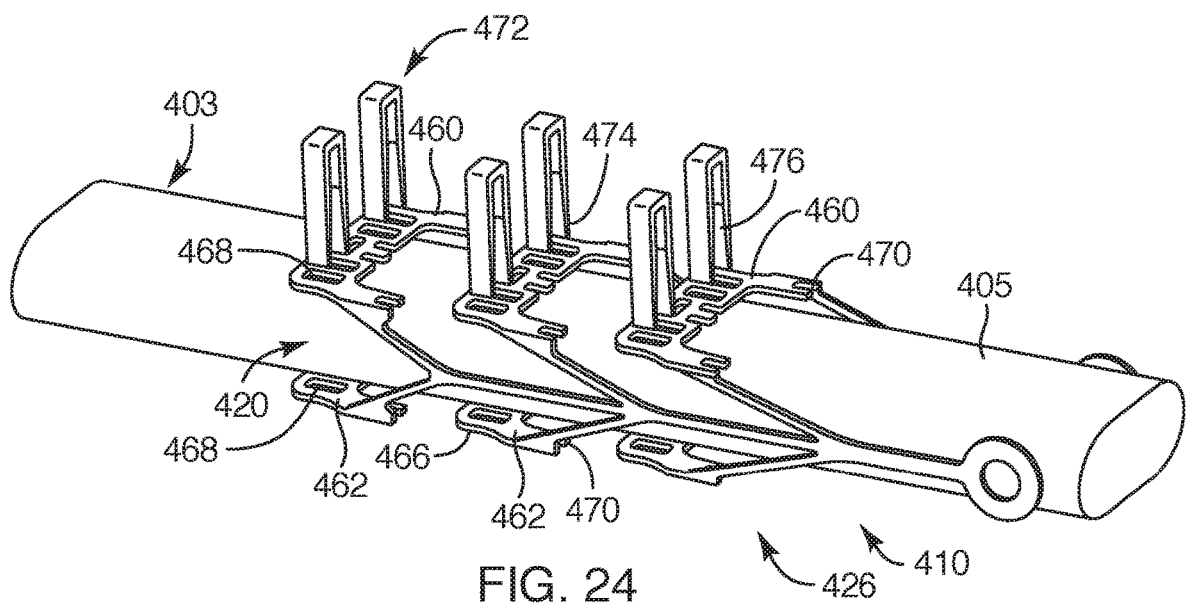
FIG. 24 is perspective view of the first part of the repair device, depicting the repair device positioned over a first tendon portion of a lacerated tendon and staples in a non-stapled position, according to another embodiment of the present invention.

With reference to FIG. 24, the first part 426 of the repair device 410 positioned over the first tendon portion 405 is depicted with staples 472 in a non-stapled position. Once the first tendon portion 405 is pulled through the bore 420 of the first part 426 of the repair device 410, the repair device 410 may be anchored to the lacerated tendon 403 with, for example, staples 472. The staples 472 may be applied via an applicator (not shown) with a staple cartridge (not shown) that may be integrated with the applicator. The staples 472 are depicted in a non-stapled position as if positioned in the staple cartridge. In the non-stapled position, the staples 472 may be disposed directly over the holes 468 defined in each of the upper pad portions 460. The staples 472 may include an elongated u-shaped configuration with free ends 474 and legs 476. The staples 472 may be properly aligned with the holes 468 with indents 470 or notches defined in the upper and lower pad portions 460, 462 such that the applicator/staple cartridge may include corresponding structure, such as tabs to ensure proper alignment of the repair device 410.

To anchor the repair device 410 to the lacerated tendon 403, the staple cartridge may be compressed so that the free ends 474 pass through the holes 468 in the upper pad portions 460 and continue downward, passing through the tendon 403 and through corresponding holes 468 in the lower pad portion 462. The free ends 474 may fold over along the outer surface 466 of the lower pad portions 462. With this arrangement, the repair device 410 may be coupled to the lacerated tendon 403. Once the staples 472 are in the stapled position to anchor the repair device 410 to the tendon 403, the applicator/staple cartridge (not shown) may be removed and the one or more wires 418 (FIG. 19) may be synched over the ends of the lacerated tendon 403 and held tight with swages or crimps (not shown), similar to that described and depicted in FIGS. 17 and 18 of the previous embodiment. In this manner, the repair device 410 may be anchored to the lacerated tendon 403 by employing separate and discrete components relative to the repair device, such as the staples 472.

In another embodiment, the repair device 410 may include tines extending from the inner surface 464 of the upper and lower pad portions 460, 462 of the repair device 410 to act in conjunction with the staples 472 to anchor or harness the repair device 410 to the lacerated tendon 403. In another embodiment, the repair device 410 may include tines or hooks (without the use of staples) for anchoring or harnessing the repair device 410 to the lacerated tendon 403. Further, in another embodiment, the first part 426 and the second part 427 of the repair device 410 may be formed as a single monolithic structure from a single tube, similar to that described in previous embodiments. It is also contemplated that the present invention of providing a moveable portion of the repair device to be moveable with tissue while another portion of the repair device is substantially fixed adjacent a repair site to facilitate proper healing at the repair site, but also providing the mobility for optimal tissue healing may also be applied to other structures in the body, such as tissue-to-bone and bone-to-bone structures. Such a device may include a tubular structure, a partially tubular structure, and/or a plate like structure including multiple interconnecting struts that may define a multi-cellular structure.

Figure 25:
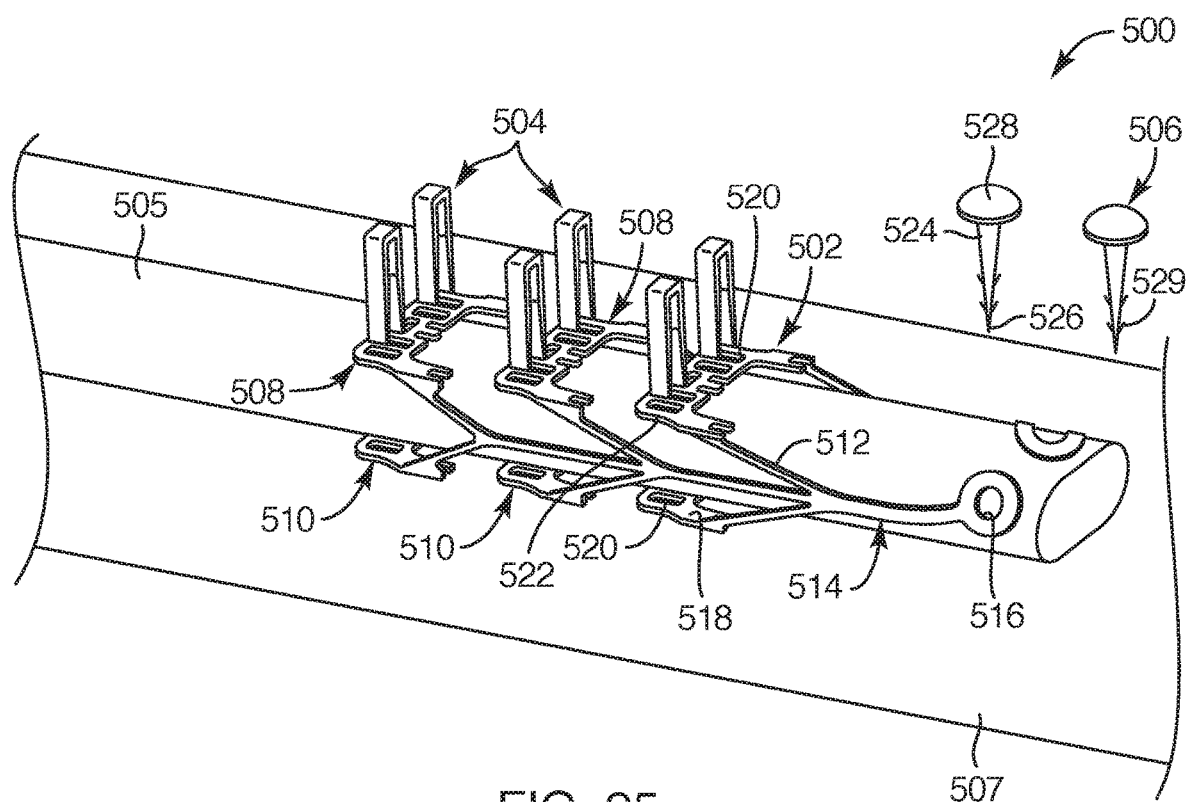
FIG. 25 is a perspective view of another embodiment of a repair device system, depicting the repair device system for fixating soft tissue, such as a tendon or ligament to bone, according to the present invention.

For example, with respect to FIG. 25, one embodiment of a repair device system 500 for fixating soft tissue 505 to bone 507 is provided (similar to the repair device depicted in FIGS. 19-24). Soft tissue 505 defined herein may be any soft tissue in the human anatomy, such as tendons and ligaments, or any other soft tissue. According to one embodiment, the repair device system 500 may include a carrier member 502, multiple anchors 504, and at least one bone anchor 506. The carrier member 502 may include upper pad portions 508 and lower pad portions 510 with multiple struts 512 coupling the upper and lower pad portions 508, 510, similar to that previously described. Further, the carrier member 502 may include one or more bone engaging portions 514, each of which may define a hole 516 or aperture therein sized to receive one bone anchor 506. The carrier member 502, including the upper and lower pad portions 508, 510, multiple struts 512, and bone engaging portions 514, may be formed seamlessly as a monolithic structure.

The carrier member 502 may be held in an open or expanded position with an applicator/anvil arrangement (not shown) similar to the open position depicted in FIG. 23. In this open position, the carrier member 502 may be in a strained position such that when released from the applicator, the carrier member 502 may automatically move to a non-strained position (or less strained than in the open position), similar to that shown in FIG. 25. The carrier member 502 may include canted micro-tines (not shown) extending from inner surfaces 518 of the upper and lower pad portions 508, 510 so that, upon positioning the soft tissue 505 between the upper and lower pad portions 508, 510, the soft tissue 505 may substantially maintain its position relative to the carrier member 502. The canted micro-tines may extend toward the one or more bone engaging portions 514.

As depicted, each pad portion of the upper pad portions 508 correspond with one of the lower pad portions 510 such that the upper and lower pad portions 508, 510 are positioned directly opposite each other on opposite sides of the soft tissue 505. Further, each of the upper and lower pad portions 508, 510 may include one or more slots 520. The term slots 520 may include apertures, holes, or notches defined through the pad portions or along a periphery 522 of the pad portions. The slots 520 defined in the pad portions may be sized and configured to receive and maintain the anchors 504 to the carrier member 502.

In one embodiment, the upper and lower pad portions 508, 510 may be substantially identical. In another embodiment, the lower pad portions 510 may include variations (relative to the upper pad portions) such that the sizing and location of the slots 520 assist in capturing the anchors 504 to the lower pad portions 510. Once the soft tissue 505 is positioned within the carrier member 502 and between the upper and lower pad portions 508, 510, as depicted in FIG. 25, the anchors 504 may be inserted and driven through the slots 520 with an anvil/cartridge arrangement (not shown).

At this stage, one or more bone anchors 506 may be inserted through holes 516 defined in the bone engaging portion 514 of the carrier member 502 and driven into the bone 507. The one or more bone anchors 506 may be inserted into pre-drilled holes formed in the bone 507. In one embodiment, each of the bone anchors 506 may include a body 524 with a pointed tip 526 and a head 528. The body 524 may include canted tines 529 extending toward the head 528 to assist in preventing migration of the bone anchor 506. In another embodiment, the one or more bone anchors 506 may be a bone screw with threads sized to be inserted in pre-drilled holes in the bone 507. In this manner, the repair device system 500 may be employed to fixate soft tissue to bone.

Figure 26:
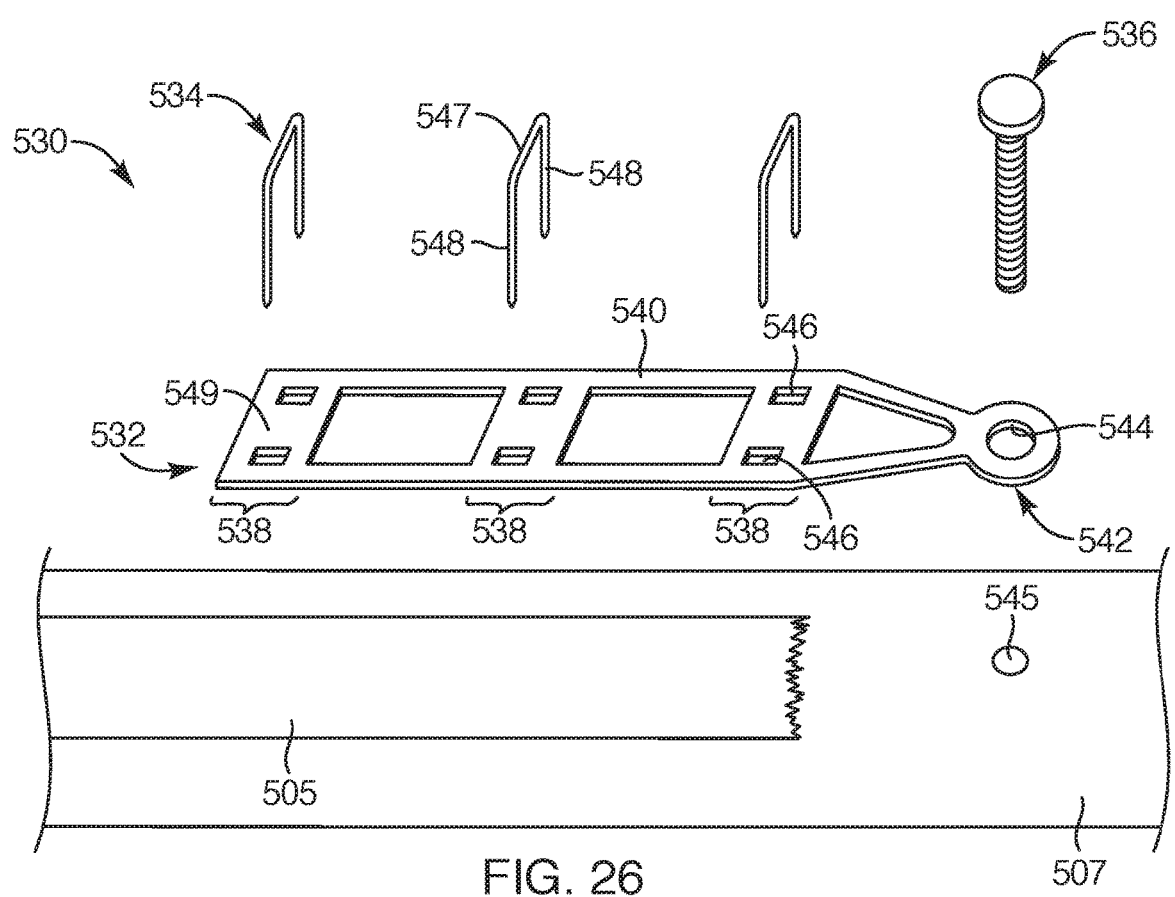
FIG. 26 is a perspective view of another embodiment of a repair device system, depicting the repair device system for fixating soft tissue, according to the present invention.
Figure 30:
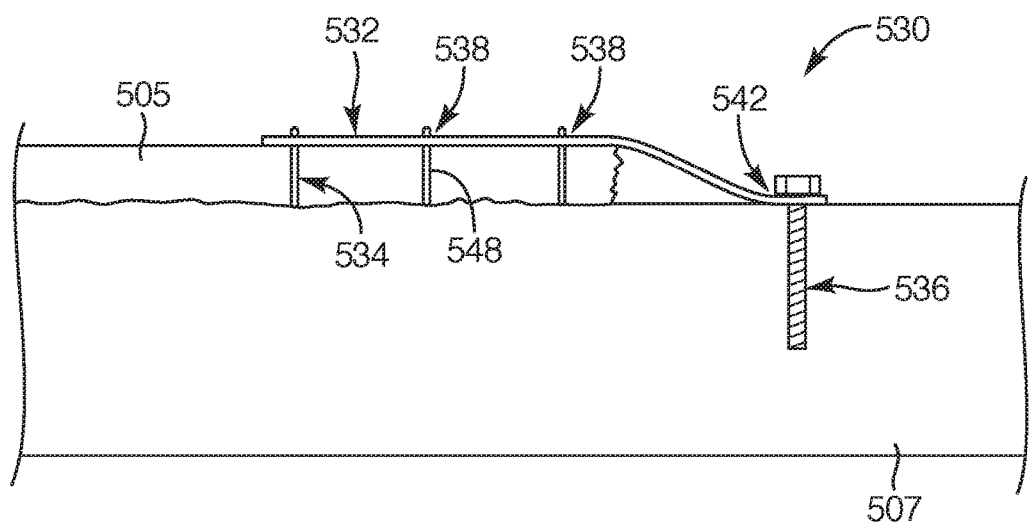
FIG. 30 is a side view of the repair device system of FIG. 26, according to another embodiment of the present invention.

Now with reference to FIGS. 26 and 30, another embodiment of a repair device system 530 for fixating soft tissue 505 to bone 507 is provided. The repair device system 530 may include a carrier member 532, multiple anchors 534, and one or more bone anchors 536. In this embodiment, the carrier member 532 may be a substantially flat member (in its pre-use position). Upon being fixated to bone 507, the carrier member 530 may deform from its substantially flat configuration (as depicted in FIG. 30). The carrier member 530 may be elongated and include a multi-cellular structure. The carrier member 530 may be a single piece, seamless, monolithic structure.

The carrier member 530 may include multiple pad portions 538 with struts 540 extending therebetween. At one end of the carrier member 532, the carrier member 532 may include a bone engaging portion 542 with a hole 544 defined therein for receiving the bone anchor 536. The multiple pad portions 538, similar to the previous embodiment, may include one or more slots 546 defined therein. The slots 546, as previously defined, may be sized and configured to receive the anchors 534. In one embodiment, each pad portion 538 may receive and correspond with one anchor 534. In another embodiment, each pad portion 538 may receive multiple anchors 534. With this arrangement, the soft tissue 505 may be positioned within, for example, a cradle/anvil arrangement (not shown). The carrier member 532 may then be positioned over the soft tissue 505 and the anchors 534 inserted through the multiple pad portions 538 with an anchor/cartridge tool (not shown). Similar to the previous embodiment, the anchors 534 may be u-shaped with a mid-upper portion 547 and legs 548, the legs extending through the slots 546 and the mid-upper portion 547 disposed over an upper surface 549 of the pad portion 538. The anvil employed with the repair device system 530 may facilitate the legs 548 of the anchors 534 to extend through the soft tissue 505, curl inward via the anvil to thereby grab and bunch the tissue within the curled anchor legs 548. Once the carrier member 532 is appropriately secured to the soft tissue 505, the bone anchor 536 may be inserted through the hole 544 of the bone engaging portion 542 and inserted into a pre-drilled hole 545 in the bone 507. The bone anchor 536 may be in the form of a bone screw or any other suitable structure to fix the carrier member 532 to the bone 507. In this manner, the repair device system 530, including a carrier member 532 having a single elongate flat configuration, may be employed to fixate soft tissue 505 to bone 507.

Figure 27:
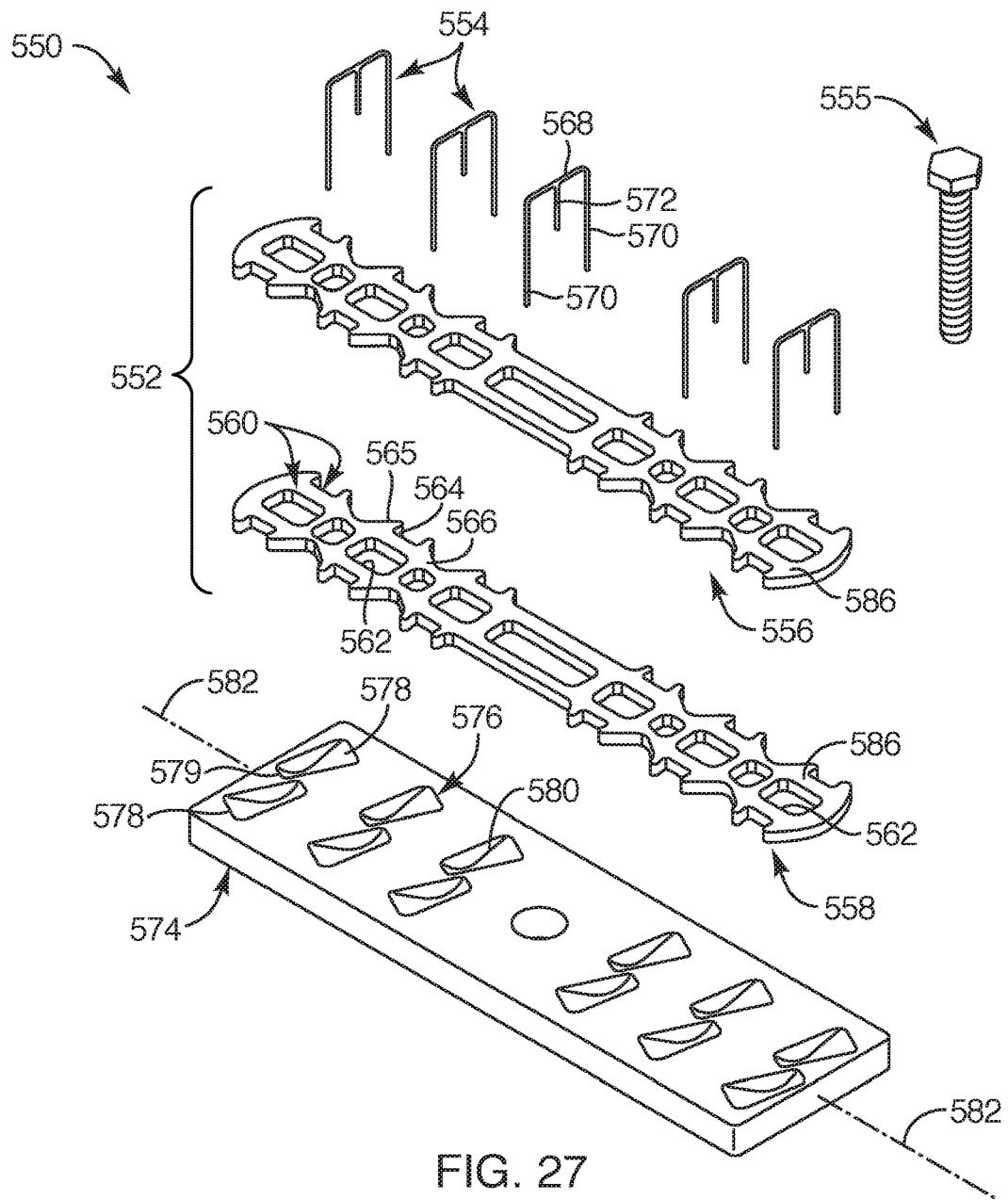
FIG. 27 is a perspective view of another embodiment of a repair device system, depicting the repair device system with upper and lower pad portions with an anvil, according to the present invention.

With respect to FIG. 27, another embodiment of a repair device system 550 for fixating soft tissue 505 to bone 507 is provided. Similar to the previous embodiments for fixating soft tissue to bone, the repair device system 550 may include a carrier member 552, multiple anchors 554, and one or more bone anchors 555. In this embodiment, the carrier member 552 may include upper pad portions 556 and lower pad portions 558, the upper pad portions 556 being separate and discrete from the lower pad portions 558. Each of the upper and lower pad portions 556, 558 may be a substantially flat structure. Further, each of the upper and lower pad portions 556, 558 may be a multi-cellular structure that may be seamless and monolithic (single piece).

As in the previous embodiments, each pad portion of the upper and lower pad portions 556, 558 may include one or more slots 560, the slots 560 being defined as apertures, holes, and/or notches. For example, the slots 560 defined in a given pad portion may include a central slot 562 and opposing side slots 564, the opposing side slots 564 being similar to a notch formed in opposing peripheral sides 565 of the pad portion. Each pad portion of the respective upper and lower pad portions 556, 558 may be interconnected to an adjacent pad portion with struts 566. Further, the central slot 562 and side slots 564 are sized and configured to receive portions of the anchors 554. The anchors 554 may be u-shaped with a mid-upper portion 568 and legs 570 extending from the mid-upper portion 568. Further, the anchors 554 may each include a tine 572 extending downward between the legs 570 and within a common plane of the legs 570.

Figure 27A:
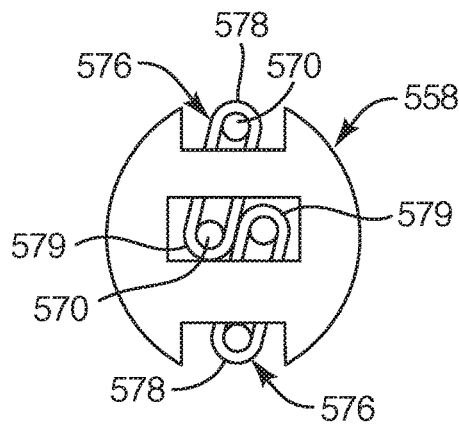
FIG. 27A is a top cross-sectional view taken above one of the lower pad portions, depicting an anchor relative to anvil beds, according to another embodiment of the present invention.
Figure 27B:
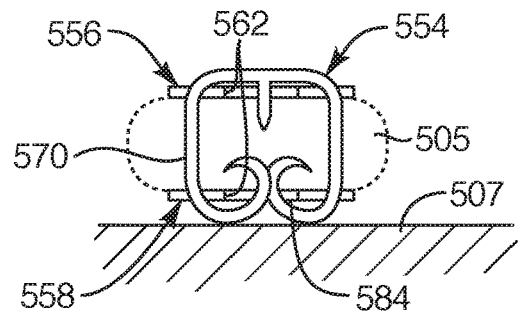
FIG. 27B is a side view of the repair device system, depicting an anchor relative to the upper and lower pad portions, according to another embodiment of the present invention.

The anchors 554 may be manipulated to engage the upper and lower pad portions 556, 558 with the soft tissue 505 therebetween, as depicted in FIGS. 27A and 27B, with an anvil 574 depicted in FIG. 27. The anvil 574 may include multiple anvil beds 576 defined therein. Each anvil bed 576 may extend from an outer end 578 to and inner end 579 with a downward slope from the outer end 578 to a ramp toward the inner end 579 of the anvil bed 576. Further, each anvil bed 576 may define a groove 580 (FIG. 27) therein to capture ends of the legs 570 and manipulate them through a precise orientation. In this manner, each anvil bed 576 extends with a radial component sized and configured to curl the legs 570 of the anchors 554. Further, in another embodiment, each anvil bed 576 may be canted relative to a longitudinal axis 582 of the anvil 574. As such, the legs 570 of the anchor 554 may be manipulated to curl and pass by each other in an over-lapping manner or side-by-side, as depicted in FIGS. 27A and 27B. With this arrangement, legs 570 of the anchor 554 may extend alongside opposing side slots 564 of the upper and lower pad portions 556, 558 and curl around a bottom surface 584 of the lower pad portions 558 and through the central slot 562 of the lower pad portions 558. Further, as depicted, each pair of the canted anvil beds 576 manipulate the legs 570 of each anchor 554 to pass through the central slot 562 so that the legs 570 grab and bundle a portion of the soft tissue 505 in a side-by-side manner. Further, the groove 580 (FIG. 27) in each anvil bed 576 facilitates a pre-determined curl in the legs 570 of the anchors 554. Such anchors 554 and carrier member 552 may be secured to the soft tissue 505 with, for example, a delivery tool having an anchor cartridge (not shown) coupled to the anvil 574.

Figure 28:
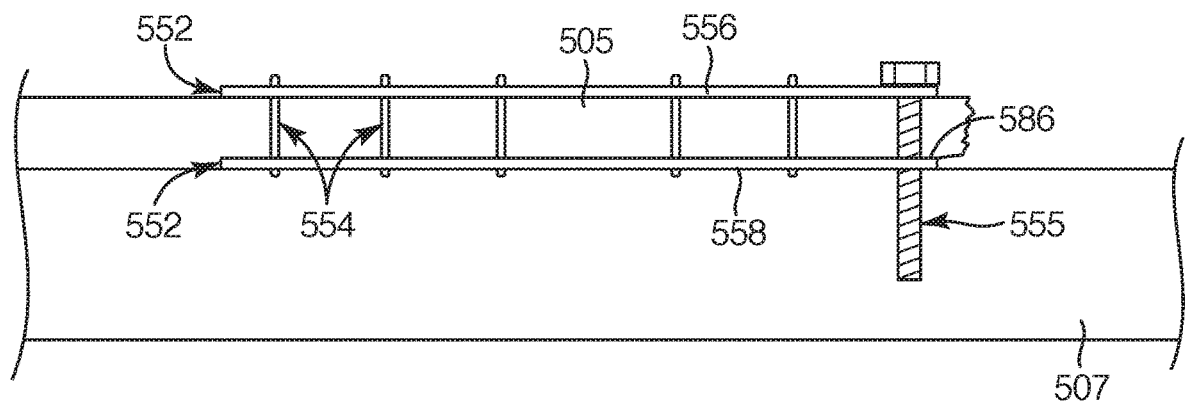
FIG. 28 is a side view of the repair device system, depicting the repair device system fixating soft tissue to bone, according to another embodiment of the present invention.

With reference to FIGS. 27 and 28, upon the anchors 554 securing the carrier member 552 to the soft tissue 505, the bone anchor 555, such as a bone screw or the like, may be inserted through, for example, the central slot 562 adjacent one end of each of the upper and lower pad portions 556, 558 and then into a pre-drilled hole in the bone 507. In one embodiment, the carrier member 552 may include a bone engaging portion 586 such that the pad portion at one common end of each of the upper and lower pad portions 556, 558 acts as the bone engaging portion 586. As such, in this embodiment, the central slot 562 at the one end of the upper and lower pad portions 556, 558 may act as the hole defined in the bone engaging portion 586 of the carrier member 552. In another embodiment, the bone engaging portion 586 may be an extension from the upper and lower pad portions 556, 558, similar to the extended bone engaging portion of FIG. 26.

Figure 29:
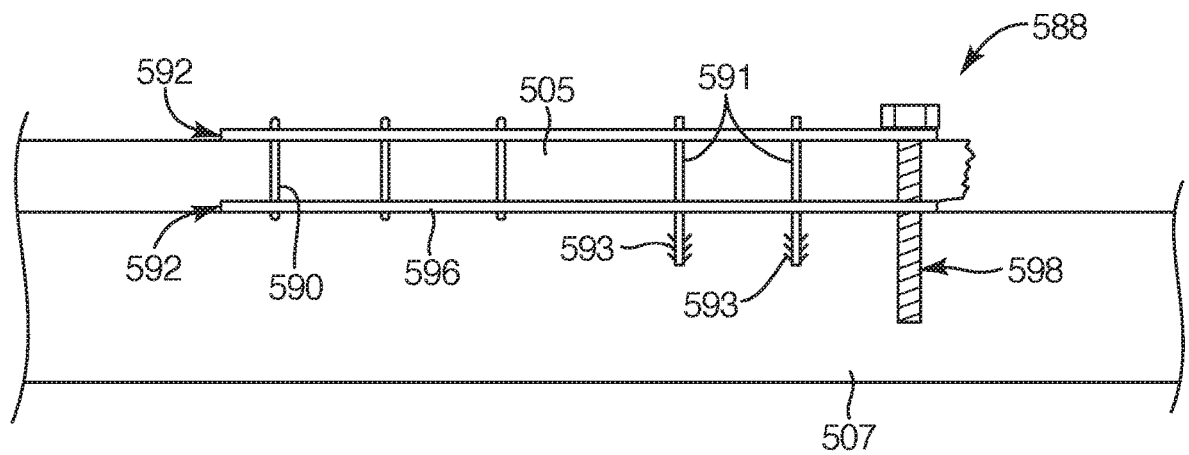
FIG. 29 is a side view of the repair device system, depicting the repair device system fixating soft tissue to bone with some of the anchors extending and fixed into the bone, according to another embodiment of the present invention.

With respect to FIG. 29, another embodiment of a repair device system 588 for fixating soft tissue 505 to bone 507 is provided. This embodiment may be similar to the repair device system 550 of FIG. 27, except the method of fixating and anchors may be different. For example, in this embodiment, one or more anchors 590 (depicted as three anchors) may be employed to secure the carrier member 592 to the soft tissue 505, as depicted in the previous embodiment. As such, the depicted three anchors 590 may wrap around the carrier member 592 and curl through the central slot 562 (FIG. 27) of the corresponding lower pad portions 596 by employing the anvil. The other anchors 591 (depicted as two anchors) may extend along the side slots 564 (FIG. 27) of the corresponding upper and lower pad portions 594, 596 (also extending through the soft tissue 505) and further extend directly into the bone 507, as depicted. Such anchors 591 may also include canted micro-tines 593 extending from each of the anchor legs to strengthen and assist securing the anchors 591 to the bone 507. To further ensure fixation of the carrier member 592 to the bone 507, a bone anchor 598, such as a bone screw, may extend through a hole (such as the central slot 562 depicted in FIG. 27) of the bone engaging portion 599, similar to the previous embodiment. In this manner, the repair device system 588 with additional bone engaging anchors 591 may be employed to fixate soft tissue 505 to bone 507.

Figure 31:
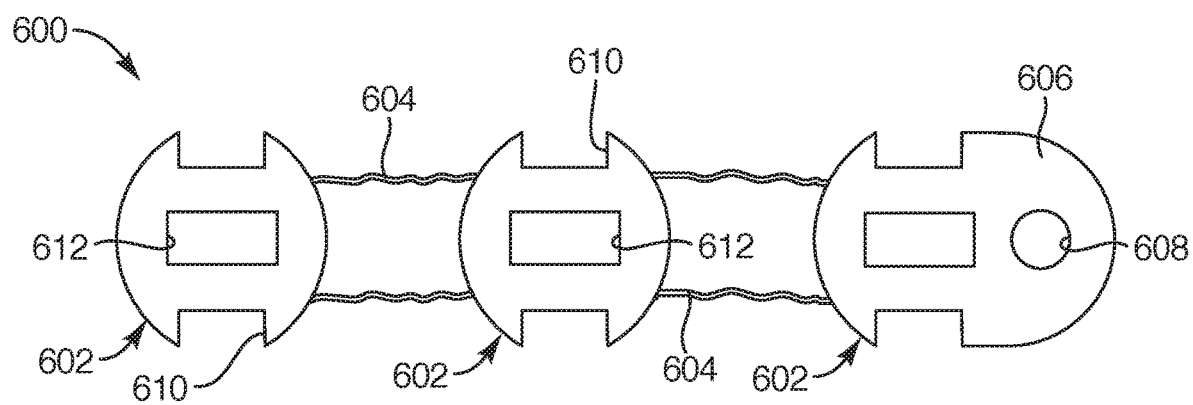
FIG. 31 is a top view of another embodiment of multiple pad portions, depicting the multiple pad portions coupled together with at least one filament, according to the present invention.

With respect to FIG. 31, another embodiment of a carrier member 600 is depicted. Such a carrier member 600 may be employed with the anchors and one or more bone anchors of the repair device systems similar to that described in previous embodiments. In this embodiment, the carrier member 600 may include multiple pad portions 602 interconnected to each other with one or more filaments 604, rather than interconnected with struts as described in previous embodiments. The one or more filaments 604 may be polymeric and/or metallic. The one or more filaments 604 may be coupled to the multiple pad portions 602 with hooks, protrusions, and/or apertures (not shown). Further, the carrier member 600 may include a bone engaging portion 606 defining a hole 608 therein for receiving a bone anchor.

In one embodiment, the carrier member 600 may include a single aligned structure of the multiple pad portions 602, separate and discrete from each other and interconnected with the at least one filament. In this embodiment, anchors may fixate each of the multiple pad portions 602 to one side of soft tissue, similar to that depicted in FIGS. 26 and 30. The anchors may be employed with the anvil 574 (FIG. 27) and may extend along side slots 610 defined in each pad portion and through the tissue and curl back into the tissue at the opposite side of the soft tissue.

In another embodiment, the carrier member 600 depicted in FIG. 31 may include two aligned structures each with multiple pad portions 602, similar to the before-described upper and lower pad portions, described relative to FIG. 27. In other words, the upper and lower pad portions, each having pad portions 602 separate and discrete relative to each other and coupled together with at least one filament 604, may be positioned along opposite sides of soft tissue in conjunction with the anvil. Anchors may then be inserted along side slots 610 of both the upper and lower pad portions and manipulated, via the anvil as described previously, through the central slot 612 of the corresponding pad portions 602 of the lower pad portion.

Figure 32:
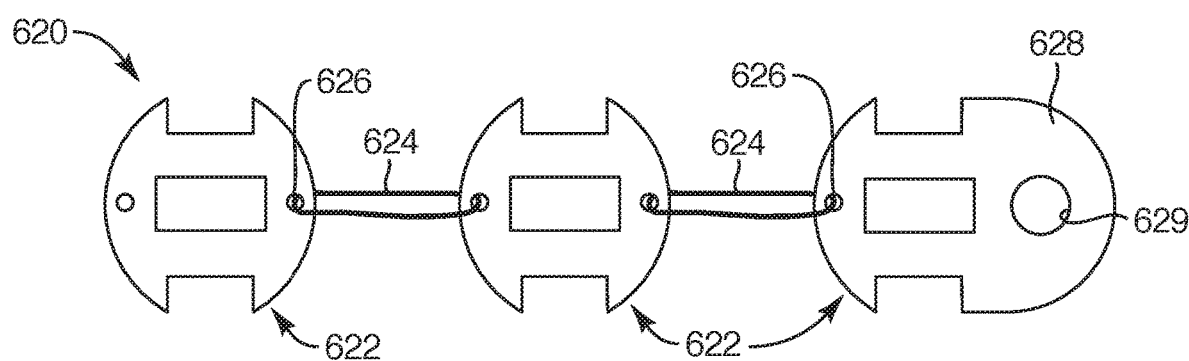
FIG. 32 is a top view of another embodiment of multiple pads portions, depicting the multiple pad portions coupled together with one or more looped filaments, according to the present invention.

In another embodiment, as depicted in FIG. 32, a carrier member 620 may include multiple separate and discrete pad portions, similar to the carrier member 600 of FIG. 31. In this embodiment, each of the pad portions 622 may be coupled to an adjacent pad portion 622 with a filament 624, such as a looped filament. The filament 624 may be separate and discrete from other filaments that couple adjacent pad portions 622. Further, each of the pad portions 622 may include apertures 626 for coupling the filaments 624 thereto. As in the previous embodiment, the carrier member 620 may include a single aligned structure of multiple pad portions 622 for coupling to a single side of soft tissue or, the carrier member 620 may include upper and lower pad portions for coupling to opposite sides of soft tissue. The carrier member 620 may be fixed to bone employing a bone engaging portion 628 and hole 629 arrangement, similar to the previous embodiment.

Figure 33:
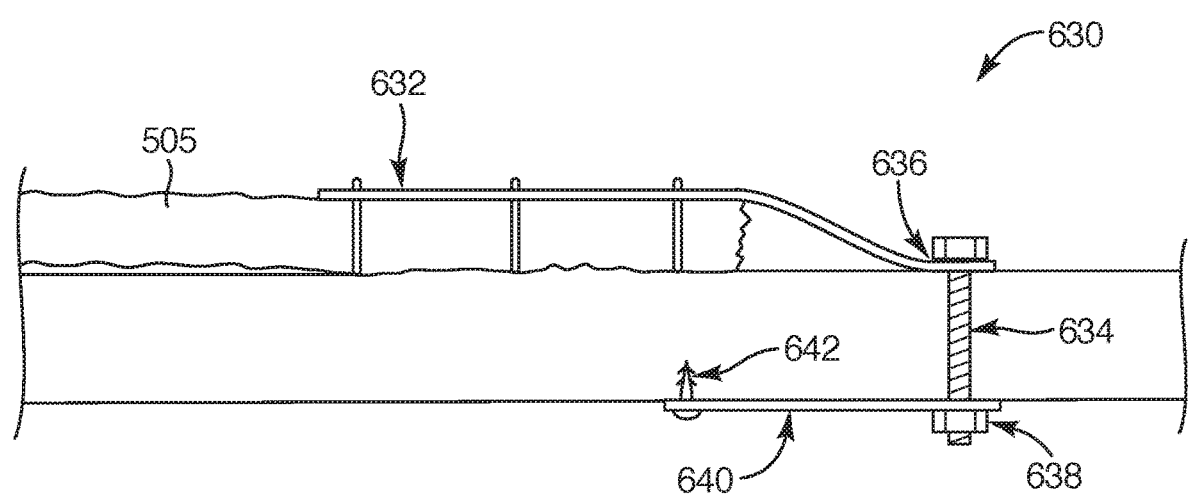
FIG. 33 is a side view of another embodiment of a repair device system, depicting a bone anchor extending through the entire bone and fixated thereto, according to the present invention.

With respect to FIG. 33, another embodiment of a repair device system 630 is depicted. In this embodiment, the repair device system 630 may include a carrier member 632 similar to any one of the carrier members previously described for fixating soft tissue 505 to bone 507. However, in instances where there is less bone 507 and the physician desires to ensure fixation to the bone 507, the physician may drill a hole entirely through the bone 507, as depicted. In this embodiment, the bone screw 634 may extend through the hole defined in the bone engaging portion 636 of the carrier member 632 and through the drilled hole of the bone 507 to be captured by a fixation member 638 at generally an opposite side of the bone 507 or carrier member 632. The bone screw 634 may be threaded to internal threads of the fixation member 638. In another embodiment, to further ensure fixation to the bone 507, there may be a second bone engaging portion 640 having an elongate structure with first and second apertures defined adjacent to opposite ends of the elongate structure. The bone screw 634 may extend through the first aperture and then captured by the threaded fixation member 638. A second bone anchor 642 may then extend through the second aperture of the second bone engaging portion 640. In this manner, upon fixating soft tissue 505 to relatively smaller sized bone 507, the physician may drill through the entire bone 507 to employ the above-described fixation member 638 to the bone screw 634 and may, in addition, ensure further fixation by employing the second bone engaging portion 640/second bone anchor 642 arrangement.

The carrier member, as disclosed in the various embodiments herein, may be formed of a polymeric material or a metallic material, such as Nitinol, steel, or titanium, or any other suitable biocompatible material known to one of ordinary skill in the art. Further, the carrier member may be formed of a bioresorbable material, such as a bioresorbable polymeric or metallic material, such as magnesium. Furthermore, the carrier member may be manufactured utilizing processes and techniques known to one of ordinary skill in the art, such as laser cutting, chemical etching and polishing processes, heat-setting techniques, stamping, or any other suitable method of manufacturing known in the art. Likewise, the anchors and bone anchors may be formed of a polymeric material or metallic material, such as steel, titanium, magnesium, or alloys thereof, or any other suitable material known in the art. Further, the anchors may be laser cut from, for example, a flat sheet of metallic material or formed using other suitable techniques known in the art.

Other examples of soft tissue repair devices, methods, and systems are set forth in U.S. patent application Ser. No. 12/783,507, filed on May 19, 2010, entitled TISSUE FIXA- TION, and U.S. patent application Ser. No. 13/021,653, filed on Feb. 4, 2011, entitled TISSUE STABILIZATION SYSTEM, and U.S. patent application Ser. No. 13/021,651, filed Feb. 4, 2011, entitled SYSTEM FOR TISSUE FIXATION TO BONE, the disclosures of which are incorporated by reference herein in their entirety.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes employing any portion of one embodiment with another embodiment, all modifications, equivalents, and alternatives falling within the spirit and scope of the invention as defined by the following appended claims.

What is claimed is:

1. A repair device system for fixating soft tissue to bone, comprising:
   a first carrier member and a second carrier member, the first carrier member being separate and discrete relative to the second carrier member, the first and second carrier members being elongated structures with multiple slots defined therein, the first carrier member and the second carrier member extending to define a first longitudinal length and a second longitudinal length, respectively, the first and second carrier members configured to be positioned along opposite sides of the soft tissue; and
   multiple anchors each being separate and discrete from the first and second carrier members, the multiple anchors each including at least two legs extending from a base such that the at least two legs are configured to be moveable from a straight position to a curled position the base of each of the anchors defining an elongated length, each of the anchors sized and configured to extend through and along the slots defined in both the first and second carrier members and through the soft tissue such that the elongated length of the base is oriented to be substantially perpendicular relative to both the first and second longitudinal lengths of the first and second carrier members, respectively, so that, upon the at least two legs of the anchors being moved to the curled position, the at least two legs of the multiple anchors extend through the slots defined in both the first and second carrier members so as to wrap around portions of one of the first and second carrier members so as to couple the first carrier member to the second carrier with the soft tissue therebetween.

2. The repair device system of claim 1, wherein at least one of the first and second carrier members comprises a bone coupling portion, the bone coupling portion being adjacent one end of the at least one of the first and second carrier members.

3. The repair device system of claim 2, further comprising a bone anchor, the bone anchor configured to be coupled to the bone coupling portion and configured to be secured to the bone.

4. The repair device system of claim 1, wherein the multiple anchors comprise a u-shaped configuration.

5. The repair device system of claim 1, wherein each of the first and second carrier members are flat monolithic structures.

6. The repair device system of claim 1, wherein the first and second carrier members extend with flat multi-cellular structures.

7. The repair device system of claim 1, wherein the slots defined in each of the first and second carrier members comprise at least one of holes and notches extending through opposing surfaces of each of the first and second carrier members.

8. A repair device system for fixating soft tissue, the repair device system comprising:
   an elongated flat first carrier member extending to define a first longitudinal length, the elongated flat first carrier member including multiple first slots defined therein;
   an elongated flat second carrier member extending to define a second longitudinal length, the elongated flat second carrier member including multiple second slots defined therein; and
   multiple anchors each being separate and discrete from the elongated flat first and second carrier members, the multiple anchors each including two legs extending from a base such that the two legs are configured to be moveable from a straight position to a curled position, the base of each of the anchors defining an elongated length, each of the anchors sized and configured to extend through and along the first and second slots defined in the respective first and second carrier members and through the soft tissue such that the elongated length of the base is oriented to be substantially perpendicular relative to both the first and second longitudinal lengths of the respective first and second carrier members, respectively, so that, upon the two legs of the anchors being moved to the curled position, the two legs of the multiple anchors extend through the first slots of the first carrier member and extend through the second slots of the second carrier member and further extend to curl and wrap around portions of the second carrier member so as to couple the first carrier member to the second carrier with the soft tissue therebetween.

9. The repair device system of claim 8, wherein the multiple anchors comprise a u-shaped configuration.

10. The repair device system of claim 8, wherein the multiple anchors each extend with the two legs with a tine therebetween.

11. The repair device system of claim 8, wherein each of the elongated flat first and second carrier members are separate and discrete relative to each other.

12. The repair device system of claim 8, wherein each of the elongated flat first and second carrier members are monolithic structures.

13. The repair device system of claim 8, wherein each of the elongated flat first and second carrier members extend with multi-cellular structures.

14. The repair device system of claim 8, wherein the first and second slots defined in each of the respective elongated flat first and second carrier members comprise at least one of holes and notches extending through opposing surfaces of each of the elongated flat first and second carrier members.

15. The repair device system of claim 8, wherein at least one of the elongated flat first and second carrier members comprises a bone coupling portion, the bone coupling portion being adjacent one end of the at least one of the elongated flat first and second carrier members.

16. The repair device system of claim 15, further comprising a bone anchor, the bone anchor configured to be coupled to the bone coupling portion and configured to be secured to the bone.

* * * * *